(12) United States Patent
Discenzo

(10) Patent No.: US 6,196,057 B1
(45) Date of Patent: Mar. 6, 2001

(54) INTEGRATED MULTI-ELEMENT LUBRICATION SENSOR AND LUBRICANT HEALTH ASSESSMENT

(75) Inventor: Frederick M. Discenzo, Brecksville, OH (US)

(73) Assignee: Reliance Electric Technologies, LLC, Thousand Oaks, CA (US)

( * ) Notice: Subject to any disclaimer, the term of this patent is extended or adjusted under 35 U.S.C. 154(b) by 0 days.

(21) Appl. No.: 09/300,645

(22) Filed: Apr. 27, 1999

Related U.S. Application Data

(63) Continuation-in-part of application No. 09/054,117, filed on Apr. 2, 1998, now Pat. No. 6,023,961.

(51) Int. Cl.$^7$ .......................... G01N 27/16; G01N 33/26; G01N 33/16; G08B 17/10

(52) U.S. Cl. ...................... 73/54.01; 73/53.01; 73/23.21; 422/82.01

(58) Field of Search .................... 73/54, 53.01, 53.05, 73/61.71, 23.2, 23.21, 23.34, 23.31, 23.3; 422/68.1, 90, 82.01

(56) References Cited

U.S. PATENT DOCUMENTS

| | | | |
|---|---|---|---|
| 2,837,913 | * | 6/1958 | Rich et al. ............................... 73/59 |
| 3,256,741 | * | 6/1966 | Wise ...................................... 73/432 |
| 3,479,863 | * | 11/1969 | Kleiss .................................... 73/54 |
| 3,526,127 | * | 9/1970 | Sarkis .................................... 73/64 |
| 3,548,637 | * | 12/1970 | Wicks, III .............................. 73/53 |
| 3,977,234 | * | 8/1976 | Lynch et al. ........................... 73/53 |
| 3,982,422 | * | 9/1976 | Harrison et al. ....................... 73/53 |
| 4,072,045 | * | 2/1978 | Kopito ................................... 73/54 |
| 4,184,364 | * | 1/1980 | Du Bae ................................... 73/54 |
| 4,200,541 | | 4/1980 | Kinner et al. ......................... 252/12.2 |
| 4,269,604 | * | 5/1981 | Snowden, Jr. .................. 23/230 HC |
| 4,457,161 | * | 7/1984 | Iwanaga et al. ........................ 73/23 |
| 4,542,640 | * | 9/1985 | Clifford ................................. 73/23 |
| 4,675,662 | | 6/1987 | Kondo et al. ......................... 340/631 |
| 4,770,027 | * | 9/1988 | Ehara et al. ............................ 73/23 |
| 4,782,332 | | 11/1988 | Cipris et al. ......................... 340/603 |
| 4,792,791 | | 12/1988 | Cipris et al. ......................... 340/603 |
| 4,798,738 | | 1/1989 | Yafuso et al. .......................... 427/2 |
| 4,818,348 | * | 4/1989 | Stetter .................................... 204/1 |
| 4,869,874 | * | 9/1989 | Falgt ..................................... 422/53 |
| 4,935,040 | | 6/1990 | Goedert ................................. 55/197 |
| 4,979,124 | * | 12/1990 | Sachse et al. ....................... 364/507 |
| 5,004,583 | | 4/1991 | Guruswamy et al. ................ 422/58 |
| 5,038,893 | | 8/1991 | Willner et al. ....................... 184/7.4 |

(List continued on next page.)

OTHER PUBLICATIONS

Berkeley MicroInstruments, Microviscometer Model BMV100.

Karagounis, et al. "A Pd–PdO Film Potentiometric pH Sensor", IEEE Transactions on Biomedical Engineering, vol. BME–33, No. 2, Feb. 1986.

*Primary Examiner*—Hezron Williams
*Assistant Examiner*—David J. Wiggins
(74) *Attorney, Agent, or Firm*—Himanshu S. Amin; John J. Horn; William R. Walbrun

(57) ABSTRACT

A multi-element fluid sensor system having a distributed sensor configuration for determining the health state of a fluid. The sensor system includes at least two sensors for collecting data relating to a particular parameter (e.g., pH, temperature, electrical conductivity, chemistry, viscosity) of the fluid. The at least two sensors may be integrated onto a semiconductor base so as to provide for a micro sensor for in situ monitoring of the fluid. The system also includes a data fusion processor operatively coupled to the at least two sensors. The data fusion processor processes the fluid data to at least compensate for information fragmentation attributed to using the at least two sensors. The data fusion processor may condense the data, combine the data, evaluate the data and interpret the data.

34 Claims, 21 Drawing Sheets

U.S. PATENT DOCUMENTS

| | | | |
|---|---|---|---|
| 5,120,421 | * 6/1992 | Glass et al. | 204/406 |
| 5,151,110 | 9/1992 | Bein et al. | 55/75 |
| 5,200,027 | 4/1993 | Lee et al. | 156/651 |
| 5,417,821 | 5/1995 | Pyke | 204/153.1 |
| 5,418,058 | 5/1995 | Li et al. | 428/327 |
| 5,469,369 | * 11/1995 | Rose-Pehrsson et al. | 364/497 |
| 5,485,491 | 1/1996 | Salnick et al. | 376/245 |
| 5,487,313 | 1/1996 | Johnson | 73/863.71 |
| 5,512,882 | * 4/1996 | Stetter et al. | 340/632 |
| 5,540,086 | * 7/1996 | Park et al. | 73/53.05 |
| 5,572,328 | 11/1996 | Fouckhardt et al. | 356/440 |
| 5,581,028 | 12/1996 | Barth et al. | 73/204.26 |
| 5,614,830 | 3/1997 | Dickert et al. | 324/553 |
| 5,633,809 | 5/1997 | Wissenbach et al. | 364/510 |
| 5,644,395 | 7/1997 | Folta | 356/246 |
| 5,654,497 | * 8/1997 | Hoffheins et al. | 73/23.2 |
| 5,660,728 | 8/1997 | Saaski et al. | 210/251 |
| 5,661,666 | 8/1997 | Pawlak | 364/571.07 |
| 5,662,165 | 9/1997 | Tubel et al. | 166/250.01 |
| 5,777,211 | * 7/1998 | Binienda et al. | 73/53.05 |
| 5,959,191 | * 9/1999 | Lewis et al. | 73/31.05 |

* cited by examiner

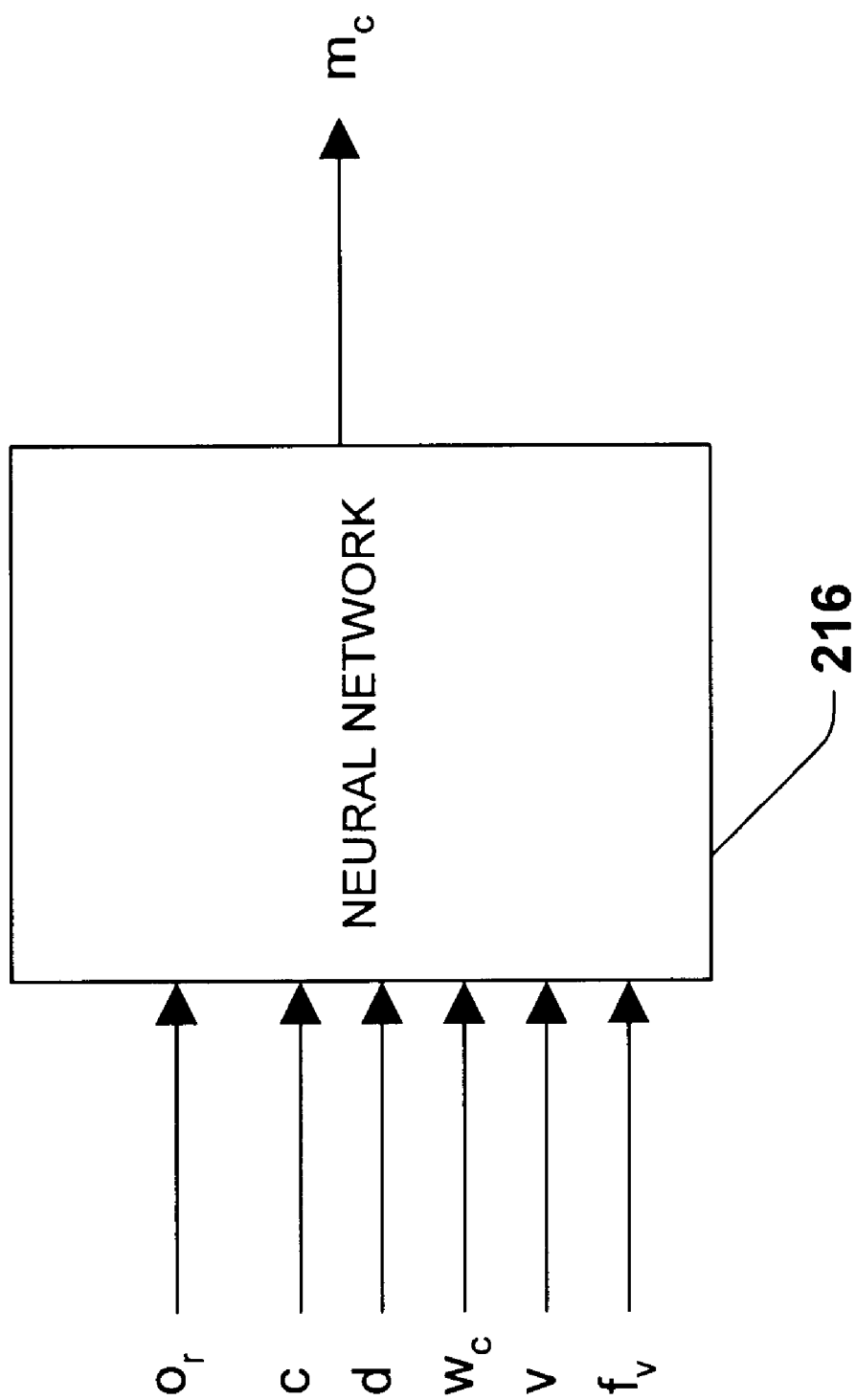

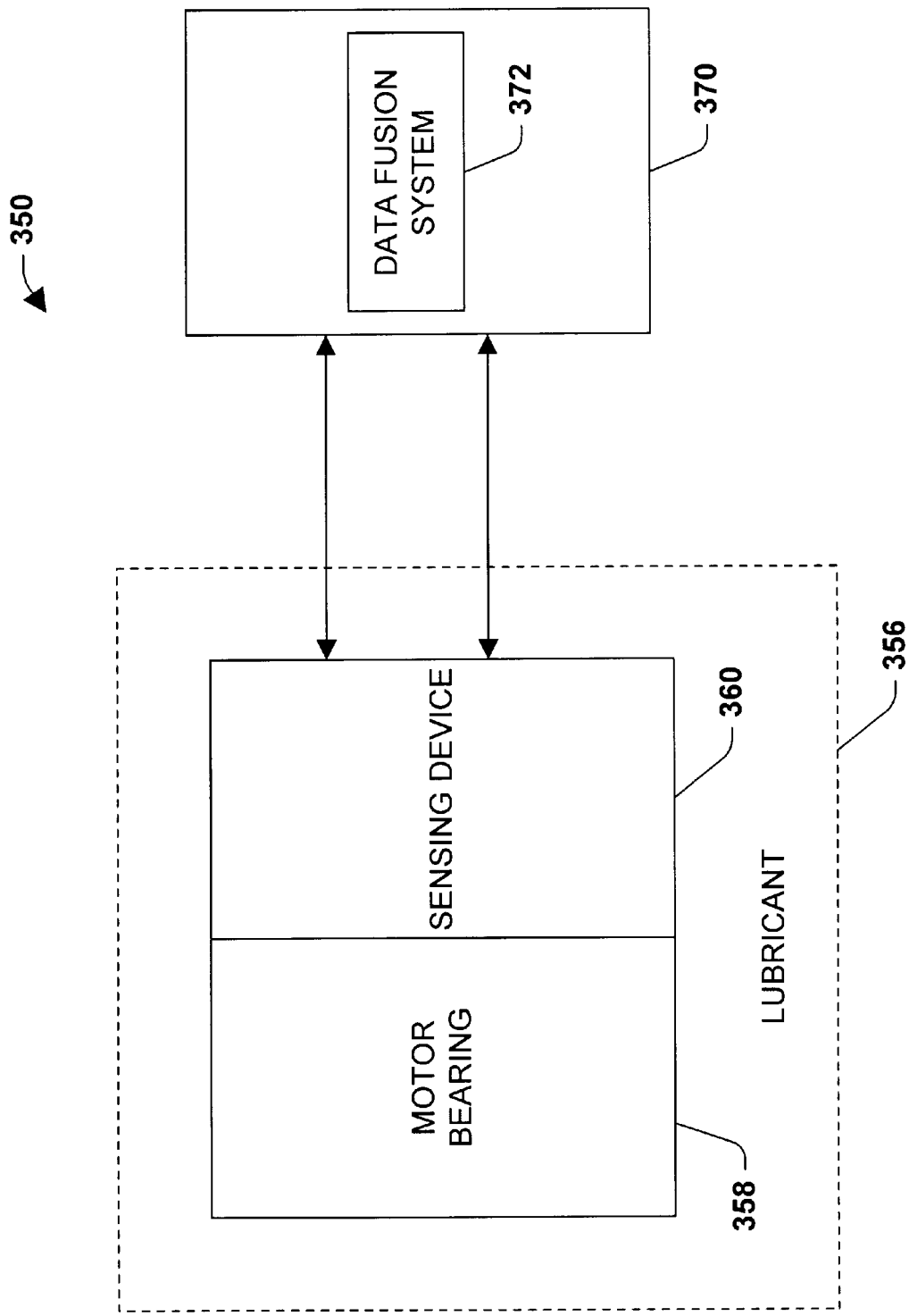

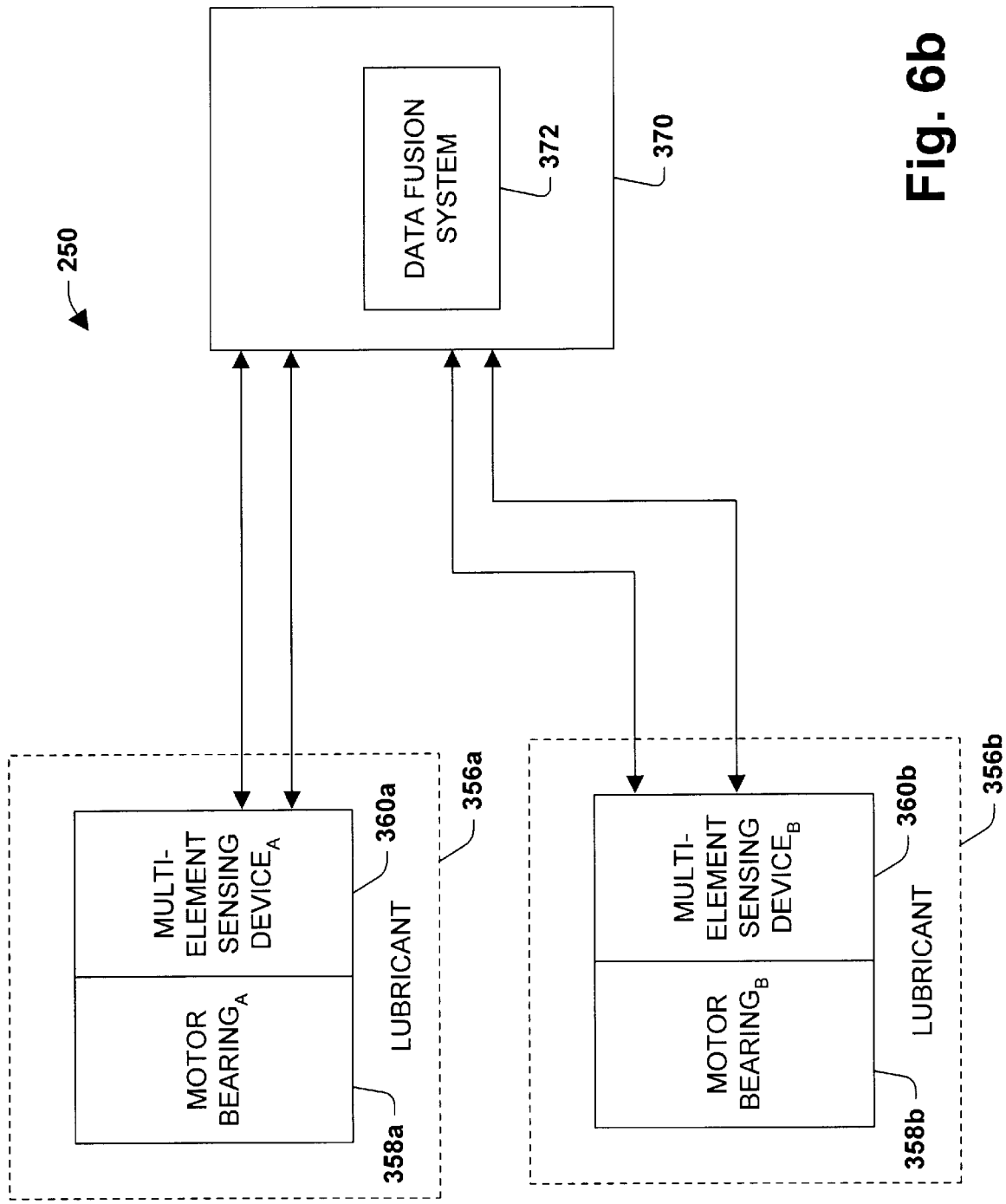

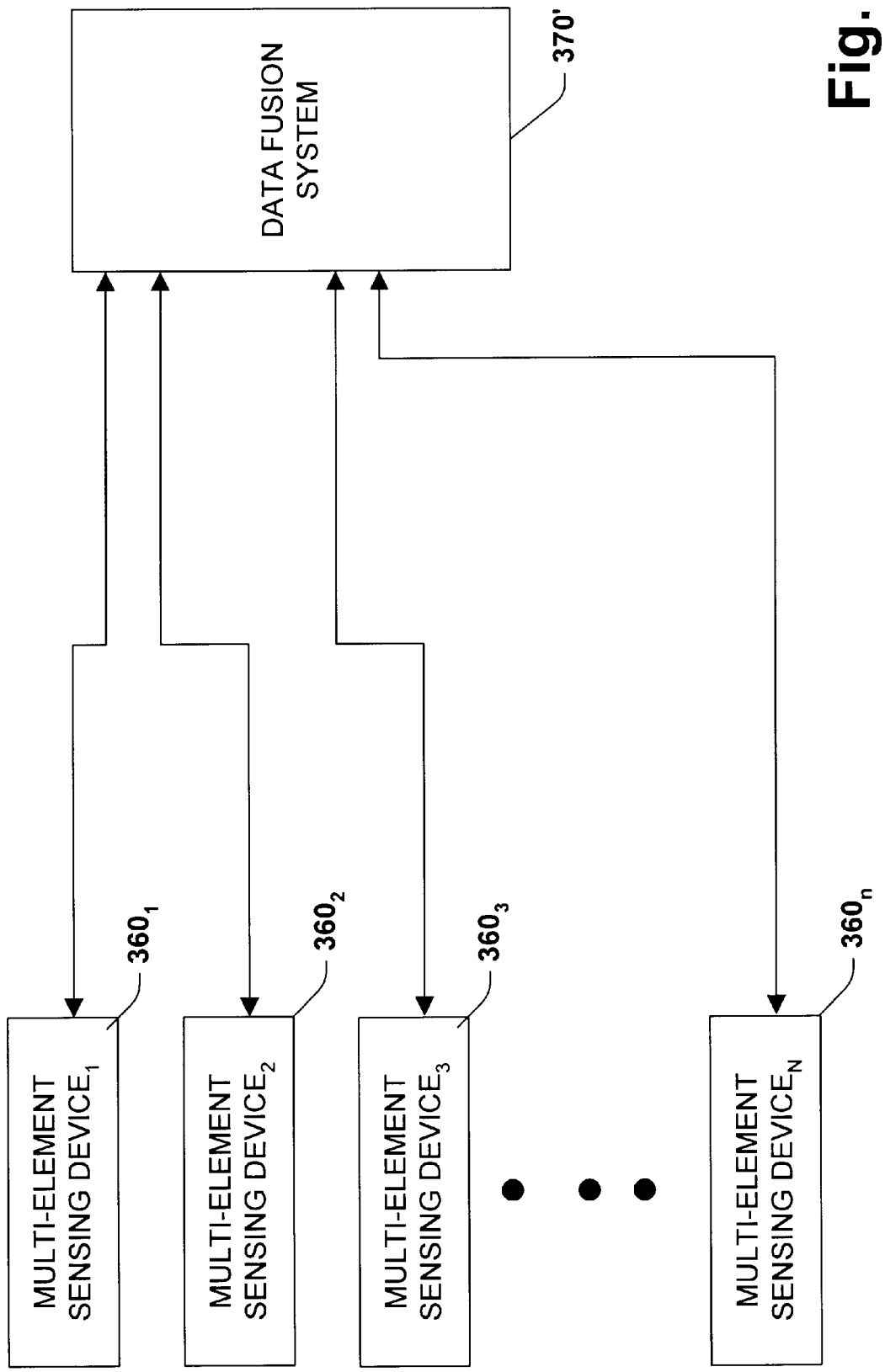

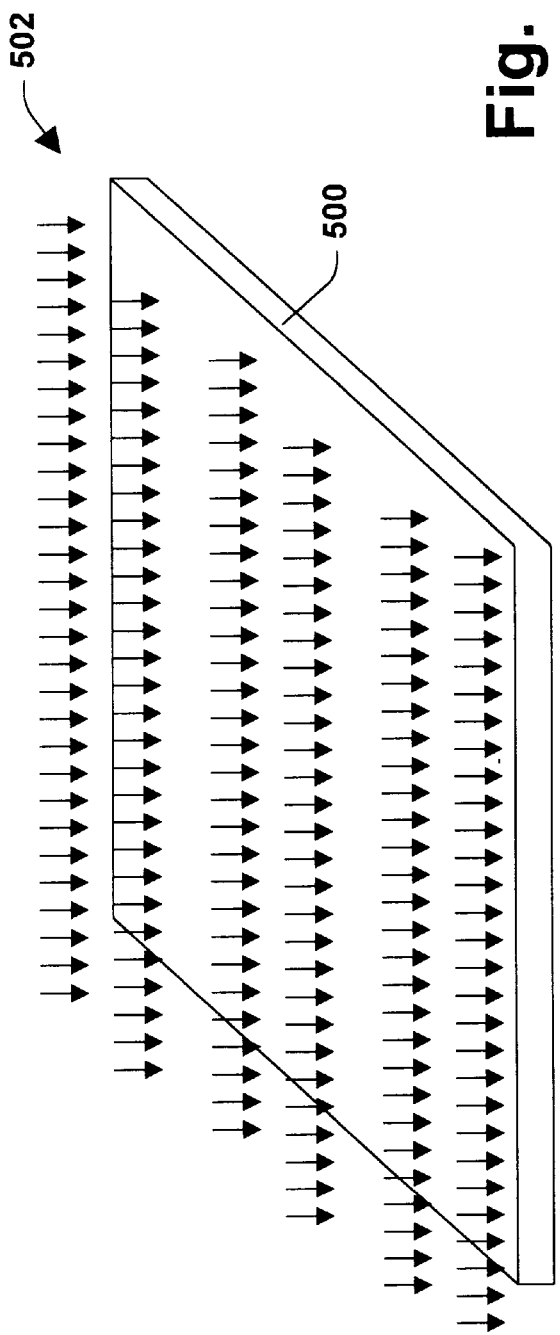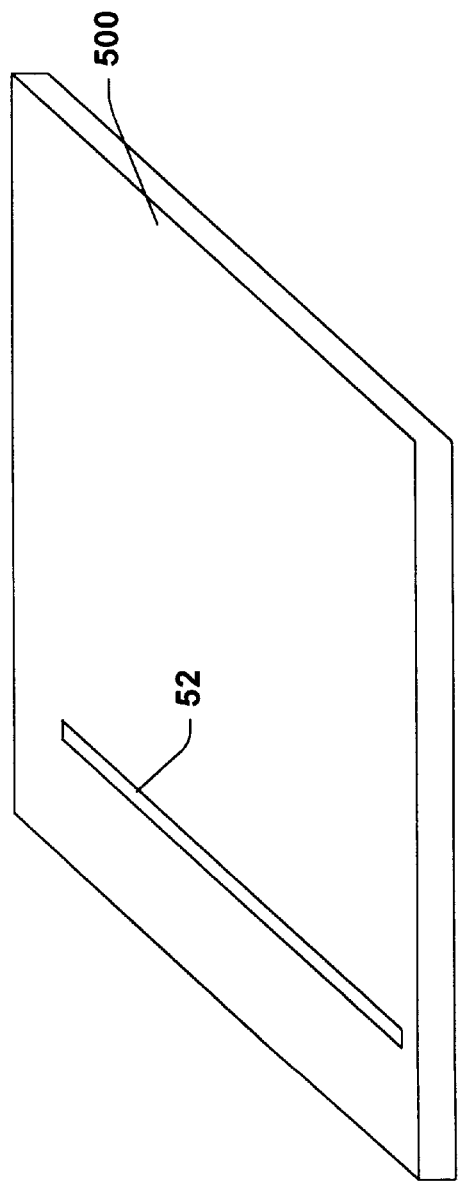

INTEGRATED MULTI-ELEMENT LUBRICATION SENSOR AND LUBRICANT HEALTH ASSESSMENT

RELATED APPLICATION(S)

This application is a continuation in part of U.S. patent application Ser. No. 09/054,117, filed Apr. 2, 1998 now U.S. Pat. No. 6,023,961 and entitled MICRO-VISCOSITY SENSOR AND LUBRICATION ANALYSIS SYSTEM EMPLOYING THE SAME, the entirety of which is incorporated herein by reference.

TECHNICAL FIELD

The present invention generally relates to an integrated multi-element lubrication sensor and health assessment system.

BACKGROUND OF THE INVENTION

Dynamoelectric machines such as motors and generators and other rotating machines such as gears and bearing systems are widely employed in industrial and commercial facilities. These machines are relied upon to operate with minimal attention and provide for long, reliable operation. Many facilities operate several hundred or even thousands of such machines concurrently, many of which are integrated into a large interdependent process or system. Like most machinery, at least a small percentage of such equipment is prone to failure. Some of such failures can be attributed to loss of lubrication, incorrect lubrication, lubrication breakdown or lubrication contamination.

Depending on the application, the failure of a machine in service can possibly lead to system or process down time, inconvenience, material scrap, machinery damage, hazardous material cleanup and possibly even a dangerous situation. Thus, it is desirable to diagnose the machinery for possible failure or faults early in order to take preventive action and avoid such problems. Absent special monitoring for certain lubrication problems, the problem may have an insidious effect in that although only a minor problem on the onset, the problem could become serious if not detected. For example, bearing problems due to inadequate lubrication, lubrication contamination or other causes may not become apparent until significant damage has occurred.

Proper lubrication facilitates the extension of machinery life. For example, when motor lubricant is continuously exposed to high temperatures, high speeds, stress or loads, and an oxidizing environment, the lubricant will deteriorate and lose its lubricating effectiveness. The loss of lubricating effectiveness will affect two main functions of a lubrication system, namely: (1) to reduce friction; and (2) to remove heat. Continued operation of such a degraded system may result in even greater heat generation and accelerated system degradation eventually leading to substantial machinery damage and ultimately catastrophic failure. To protect the motor, the lubricant should be changed in a timely fashion. However, a balance must be struck—on one hand it is undesirable to replace an adequate lubricant but on the other hand it is desired to replace a lubricant that is in its initial stages of breakdown or contamination before equipment damage occurs. Since each particular application of a lubricant is relatively unique with respect to when the lubricant will breakdown or possibly become contaminated, it becomes necessary to monitor the lubricant.

Various techniques for analyzing lubricants are known. For example, measuring a dielectric constant change in the lubricant or recording a thermal history of the lubricant have been employed for monitoring the lubricant's condition. However, these methods measure a single parameter and require the use of the same lubricant or assume no machinery malfunctions throughout the measurements. Furthermore, these monitoring techniques are generally not performed in situ and typically require that a sample of the lubricant be extracted and analyzed using laboratory grade equipment to determine the condition of the lubricant. The need to monitor and determine the current and future health of lubricants include grease and oils such as used in bearing systems for motors, gears, pillow blocks, hydrodynamic bearings as well as hydraulic fluids such as found in pumps and pump systems, and cutting fluids to name a few.

Single parameter sensors only provide a narrow view of a lubricant quality and/or health. Accurate lubricant health assessment and lifetime prediction is virtually impossible to achieve via sensing a single parameter of the lubricant. The need for more information about the lubricant is readily apparent from the many parameters which are reported in a typical laboratory report of lubricant condition.

In view of the above, there is a need for an improved sensor for detecting an operating state of a lubricant.

SUMMARY OF THE INVENTION

The present invention relates to a microfabricated integrated electrochemical and viscosity sensor. In particular, the present invention relates to an integrated multi-element lubrication sensor and health assessment system. The lubrication sensor is made using integrated circuit-like microfabrication techniques (e.g., silicon based fabrication and deposition techniques). As a result, the lubrication sensor of the present invention provides for substantial advantages in terms of performance, reduced size, weight and costs—especially since the wafer level technology employed affords for automated and batch production of numerous lubrication sensors on a single wafer. As will be described in greater detail in the foregoing discussion, the present invention also provides for integrated signal processing and sensor fusion as well as communications.

The lubrication sensor includes multiple elements (e.g., sensing devices) for sensing various characteristics of a lubricant. For example, the lubrication sensor includes a pH sensor, an electrochemical sensor, a conductivity sensor, viscosity sensor and temperature sensor. The reduced size of the lubrication sensor of the present invention provides for continuous in situ monitoring of the lubricant. In other words, the lubrication sensor of the present invention affords for monitoring the lubricant within its operating environment as compared to extracting a sample and testing the lubricant at a remote site. Signal data from each of the sensing devices is combined within a data fusion framework to obtain useful information relating to the condition of the lubricant as well as the machine and/or process employing the lubricant.

The present invention employs data fusion because of information fission which is inherent to a process relating to sensing a physical environment through several different sensor modalities. In particular, each sensing element provides a unique window into the physical environment where the phenomena to be observed is occurring. Because the complete details of the phenomena being studied (e.g., detecting the operating state of the lubricant or the process) are not contained within a single sensing element window, there is information fragmentation which results from this fission process. These information fragments associated with the various sensing devices contain both independent and dependent components. The independent components are used to further fill out (or span) the information space and the dependent components are employed in combination to improve the quality of common information recognizing that all sensor data is subject to error and noise. In this context, data fusion is algorithmic processing of sensor data to compensate for the inherent fragmentation of information because a particular phenomena may not be observed directly using a single sensing element. In other words, the data fusion architecture provides a suitable framework to facilitate condensing, combining, evaluating and interpreting the available sensed information in the context of the particular application.

Thus, the present invention provides for a micro multi-element lubrication sensor which affords in situ monitoring of a plurality of lubricant parameters. Furthermore, the present invention employs a data fusion framework and algorithms to facilitate condensing, combining, evaluating and interpreting various sensed data. The present invention also facilitates establishing a health state of a system employing the lubrication sensor of the present invention, as well as predicting a future state of the lubricant and/or system employing the lubrication sensor. Additionally, the lubrication sensor may communicate raw data, diagnostic data and state data to a remote device.

In accordance with one aspect of the present invention, a multi-element fluid sensor system includes: at least two sensors, each sensor adapted to collect data relating to a fluid; and a data fusion processor operatively coupled to the at least two sensors, the data fusion processor processing the fluid data to at least compensate for fragmentation of information attributed to using the at least two sensors.

Another aspect of the present invention relates to a fluid sensing system including: at least two sensors integrated onto a semiconductor base, the sensors respectively collecting data relating to a fluid; and a data fusion processor also integrated onto the semiconductor base and being operatively coupled to the at least two sensors, the data fusion processor processing the fluid data to at least compensate for fragmentation of the fluid data attributed to using the at least two sensors.

Yet another aspect of the present invention relates to a system for in situ monitoring of a lubricant employed in a dynamoelectric machine, including: means for collecting data for a plurality of parameters relating to the health of the lubricant; and means for fusing the data to at least compensate for fragmentation of information between the data for the plurality of parameters.

Still another aspect of the present invention relates to a method for in situ monitoring of a lubricant, including the steps of: using at least two sensors to collect data relating to the health state of the lubricant while the lubricant is being used; and using a data fusion system to process the data.

Another aspect of the present invention relates to a lubrication sensor including: at least two sensors, each sensor adapted to collect data relating to a lubricant; and a data fusion processor operatively coupled to the at least two sensors, the data fusion processor processing the lubricant data to at least compensate for fragmentation and/or overlap of information attributed to using the at least two sensors.

Still yet another aspect of the present invention relates to a lubrication sensor for use in connection with a dynamo-electric machine, including: at least two of the following sensing devices adapted to collect data relating to a lubricant: a temperature sensor for sensing temperature of the lubricant, a viscosity sensor for sensing viscosity of the lubricant, a chemical sensor for sensing chemical parameters of the lubricant, a conductivity sensor for sensing conductivity of the lubricant, a pressure sensor for sensing lubricant pressure; a fluid density sensor for sensing lubricant density; and a pH sensor for sensing lubricant pH; and a data fusion processor operatively coupled to the at least two sensing devices, the data fusion processor processing the lubricant data to at least compensate for fragmentation and/or overlap of information attributed to using the at least two sensing devices.

Another aspect of the present invention relates to a multi-element fluid sensor system, including a first sensor adapted to collect data relating to a fluid; a second sensor substantially identical to the first sensor, the second sensor providing redundancy in collecting the fluid data; and a processor operatively coupled to the first and second sensors, the data fusion processor processing the fluid data; wherein the employment of the second sensor facilitates fluid data reliability and accuracy.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 4c is a block diagram illustrating the employment of a neural network in deriving a parameter relating to lubricant operating state;

FIG. 6a is a functional schematic diagram of a motor bearing lubrication diagnostic system in accordance with one embodiment of the present invention;

FIG. 6b is a functional schematic diagram of a motor bearing lubrication diagnostic system in accordance with another embodiment of the present invention;

FIG. 6c is a functional schematic diagram of a lubrication diagnostic system for diagnosing lubrication regarding a plurality of machines in accordance with another embodiment of the present invention;

FIG. 8 is a perspective illustration of a silicon substrate undergoing deposition, photolithography and etching steps in accordance with the present invention;

FIG. 9 is a perspective illustration of the silicon substrate of FIG. 8 after formation of a pH electrode in accordance with the present invention;

DETAILED DESCRIPTION OF THE INVENTION

Figure 1:
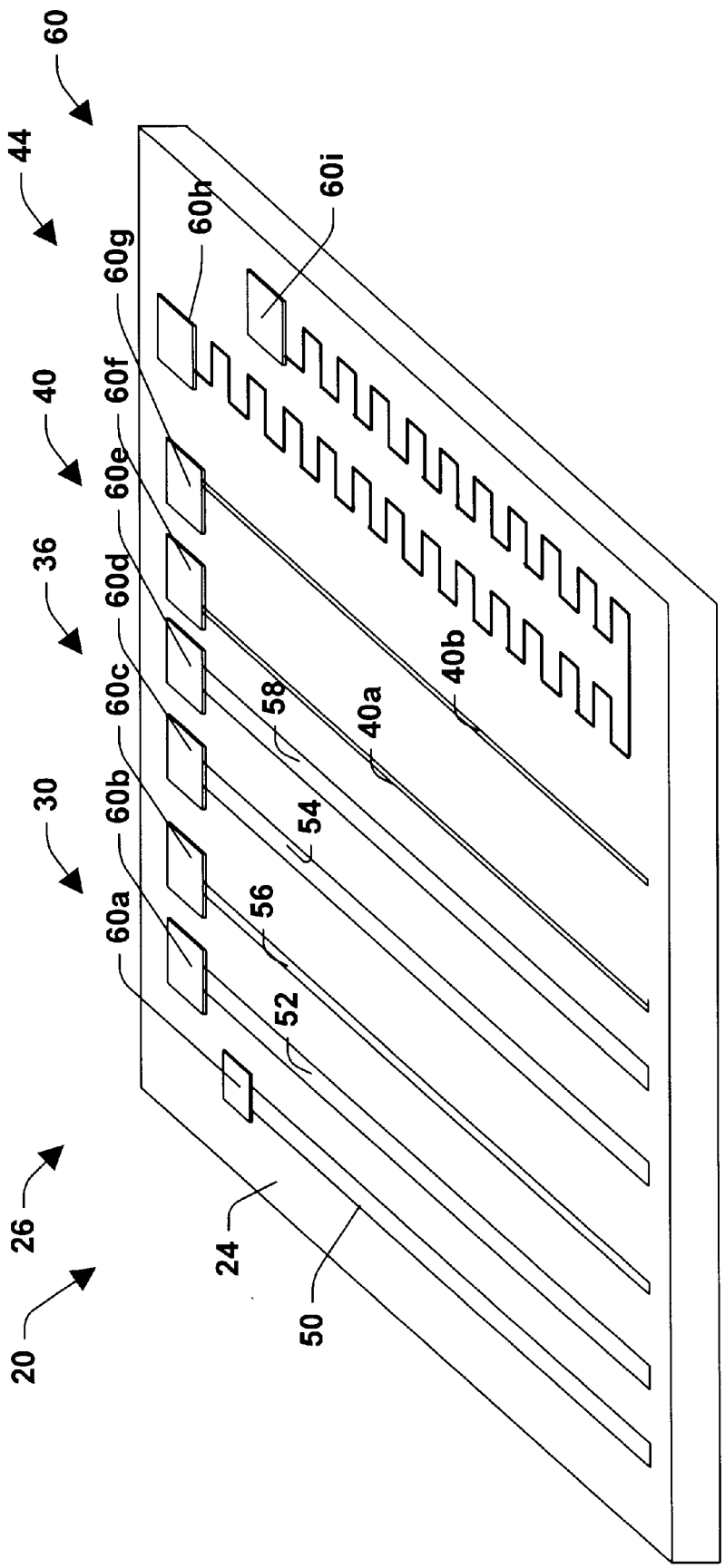
FIG. 1 is a perspective illustration of a lubrication sensor in accordance with one embodiment of the present invention.

The present invention will now be described with reference to the drawings, wherein like reference numerals are used to refer to like elements throughout.

As is mentioned above, the present invention relates to a micro electromechanical system type (MEMS-type) multi-element lubrication sensor and health assessment system. The present invention affords for in situ monitoring of a variety of fluid parameters via a plurality of sensing devices (elements). A data fusion framework is employed to facilitate condensing, combining, evaluating and interpreting the various sensed data.

Referring initially to FIG. 1 an exemplary multi-element lubrication sensor 20 in accordance with the present invention is shown in perspective view. Although the discussion herein is primarily directed to lubrication sensing, it is to be appreciated that the present invention has applicability to a variety of fluids as well such as for example hydraulic fluids, cutting fluids and biological fluids. All such suitable applications are intended to fall within the scope of the hereto appended claims.

The lubrication sensor 20 includes a semiconductor base 24 which preferably comprises silicon, however, any suitable material may be employed. Located on the surface of the base 24 are a plurality of sensing devices 26 for sensing various parameters of a lubricant. More particularly, the sensing devices 26 include a pH sensor 30 for sensing the pH of the lubricant. A chemical sensor 36 provides for sensing the chemistry of the lubricant. A conductivity sensor 40 provides for sensing the electrical conductivity of the lubricant. A temperature sensor 44 provides for sensing the temperature of the lubricant.

The pH sensor 30 includes a reference electrode 50 comprising any suitable material (e.g., Ag, AgCl) and a pH electrode 52 comprising any, suitable material (e.g., palladium-palladium oxide (Pd-PdO)). The pH sensor 30 provides for sensing the pH of the lubricant or fluid being analyzed. An exemplary discussion relating to pH sensors is found in "A Pd-PdO Film Potentiometric pH Sensor, by Karagounis et al., IEEE Transactions on Biomedical Engineering, Vol. BME-33, No. 2, February 1986 which is hereby incorporated by reference in its entirety.

The chemical sensor 36 is of a 3-electrode configuration which includes a reference electrode 54 comprising any suitable material (e.g., Ag, AgCl), a working electrode 56 (e.g. comprising Ag) and a counter electrode 58 (e.g., comprising Ag). The chemical sensor 36 is of a design typically used in conjunction with voltammetric techniques. It is to be appreciated that other suitable sensor designs including a 2-electrode electrochemical sensor, may be employed. When either an AC or DC voltammetric signal is applied to the working electrode 56, a response current is generated between the working electrode 56 and the counter electrode 58. The response current signal parameters vary depending upon the electrochemical processes occurring at the surface of the working electrode 56. The electrochemical processes are a function of the constituent concentrations, and the response current is therefore responsive to these concentrations. The electrochemical sensor is useful for determining the presence of contaminants like water or oxidation, for example, in the lubricant being analyzed.

The electrical conductivity sensor 40 is of a two electrode design, however, it is to be appreciated that other configurations (e.g., four electrode) may be employed. In the preferred embodiment, the two electrodes (40a, 40b) comprise gold, however, any suitable metal or material may be employed. Two and four electrode conductivity sensors are well known and thus further discussion related thereto is omitted for sake of brevity. Knowledge of the conductivity is also useful for determining if metal wear and/or water is contaminating the lubricant, for example.

The temperature sensor 44 provides for determining the temperature of the lubricant or fluid being analyzed, and is preferably formed from platinum, however, it is to be appreciated that any material (e.g., gold) suitable for carrying out the present invention may be employed. The temperature sensor 44 is patterned on the base 24 in accordance with a predetermined length, width and surface area. Therefore, by knowing the surface area of the temperature detector 44 and the material of which it is made, a temperature of a lubricant to which the temperature sensor 44 is exposed may be determined based on the electrical conductivity of the temperature detector 44. Knowledge of the lubricant temperature is useful in interpreting the health state of the lubricant being analyzed because certain lubricant parameters (e.g. viscosity) are a function of lubricant temperature. Furthermore, the rate of lubrication breakdown or additive depletion is also a function of temperature. Therefore, predicting the remaining useful life of the lubricant also requires temperature measurement.

Each lubricant parameter sensor (e.g. pH sensor 30, electrochemical sensor 36, conductivity sensor 40, temperature sensor 44) has respective sets of contact pads 60a–60i (collectively referred to by reference number "60") which provide for easy coupling to the respective sensors. The lubricant sensor 20 is small having a square area of approximately 4 mm. Accordingly, the lubrication sensor 20 is desirable for use in applications where space is at a premium but where accuracy, reliability, and sensitivity of measured data are also at a premium. Furthermore, because the lubrication sensor 20 is fabricated in accordance with integrated circuit-like fabrication techniques, large batches of the lubrication sensors 20 may be easily and efficiently produced with good production yields, using conventional wafer fabrication facilities.

It is to be appreciated that another set of sensing devices 26 and electrical contacts 60 may be formed on the other side of the base 24 so as to increase the functionality of the lubrication sensor 20.

Furthermore, it is to be understood that some sensing devices 26 may be omitted from the lubrication sensor 20 and/or different types of sensing devices (e.g., pressure sensor, IR sensor, light sensor, density sensor, light transmission sensor, shear sensor) may be incorporated into the lubrication sensor 20. One, some or all of the sensing devices 26 may be replicated "n" number of times (wherein "n" is an integer) on a single lubrication sensor 20. Such an embodiment may provide for increased reliability because if one particular sensing device failed there would be like sensing devices serving as backups. Multiple sensing devices of the same type on a single lubrication sensor may also afford for increased accuracy as a result of improved signal to noise ratio. The multiple versions of the same sensing element type may span a wide range of sizes, ratios, etc., each of which has a range of optimal sensing accuracy. Together these sensor elements 26 provide for substantial accuracy over a wide range of parameter values. The replicated sensing devices 26 may also improve dynamic range of the lubrication sensor 20 as well as versatility (e.g., the lubrication sensor may be employed on a wide range of materials and/or fluids). Such an embodiment may also have enhanced integrity because it may be able to sense if a particular sensing device 26 has failed or to identify the type of contaminant (e.g., engine coolant, transmission fluid).

Figure 2:
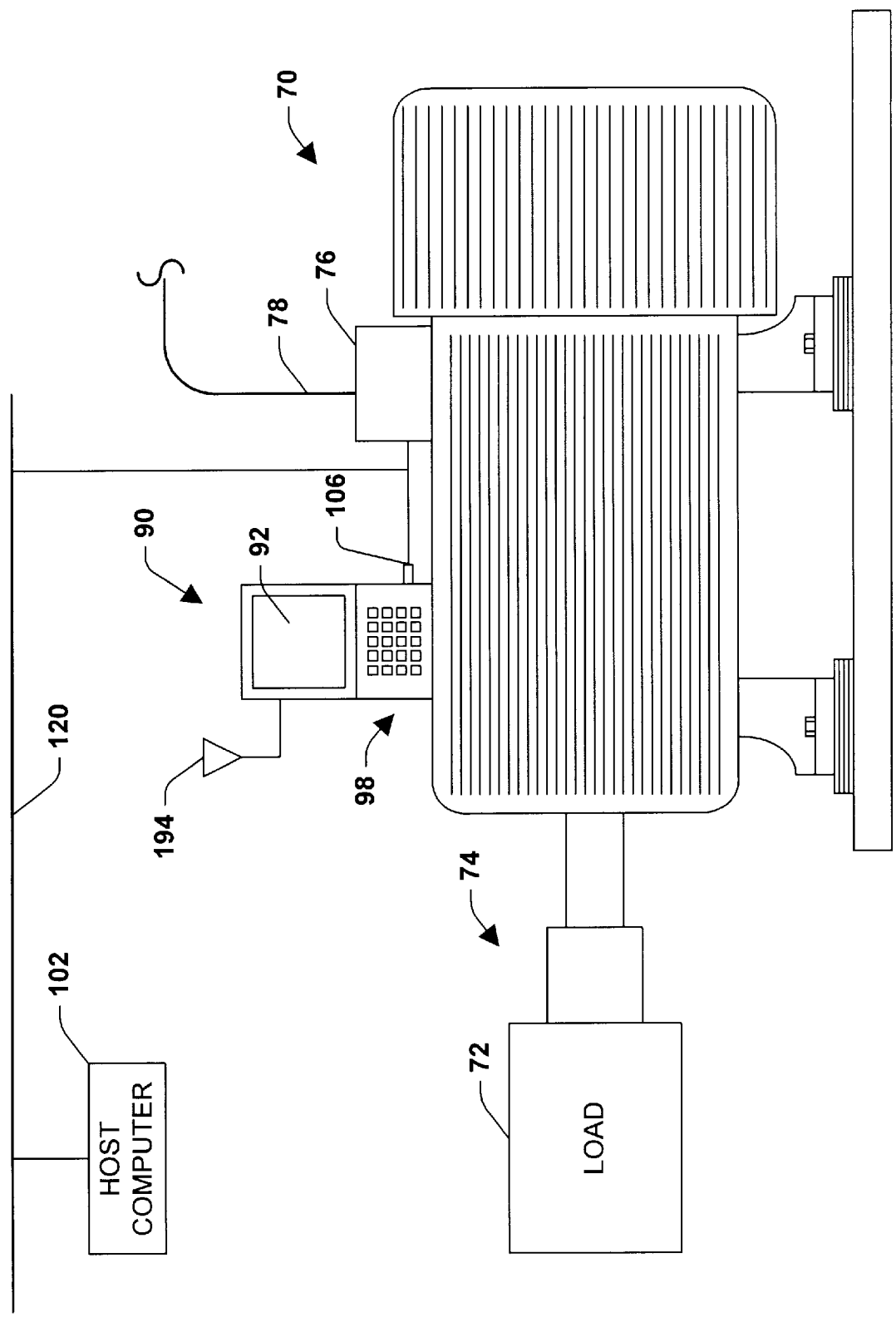
FIG. 2 is a functional schematic diagram of an integrated AC induction motor and lubrication analyzer employing the lubrication sensor of FIG. 1 in accordance with the present invention.

Turning now to FIG. 2, an exemplary environment in which the present invention may be employed is shown. A three-phase AC induction motor 70 is depicted driving a load 72 through a shaft coupling 74. The motor 70 includes a junction box 76 for receiving conductors from power lines via a conduit 78, which are tied to power supply lines (not shown) of the motor 70. The motor 70 is AC powered and operates at an AC power line frequency of 60 Hz. However, it is appreciated that different line frequencies (e.g., 50 Hz) may be employed. Coupled to the motor 70 is a lubrication analyzer 90 (FIG. 3) which as will be discussed in greater detail below provides for receiving and processing data relating to the health of lubricant employed by the motor 70.

The lubrication analyzer 90 includes a display 92 for displaying to an operator information relating to the health of the lubricant. It is to be appreciated that the lubrication analyzer 90 may also perform other functions relating to determining the health of the motor 70 (e.g., current signature analysis, vibration analysis, etc.). The lubrication analyzer 90 further includes an operator input device 98 in the form of a key pad which enables a user to enter data, information, function commands, etc. as is conventional. For example, the user may input information relating to lubricant type via the keypad 98 for subsequent transmission to a host computer 102. In addition, the keypad 98 may include up and down cursor keys for controlling a cursor which may be shown on the display 92. The lubrication analyzer 90 includes a communications port 106 for interfacing the lubrication analyzer 90 with the lubrication sensor 20 (FIG. 3) and the host computer 102 via a suitable communications link.

According to an embodiment of the present invention, the lubrication analyzer 90 is part of a distributed communication system including a network backbone 120. The network backbone 120 may be a hardwired data communication path made of twisted pair cable, shielded coaxial cable or fiber optic cable, for example, or may be wireless or partially wireless in nature. Information is transmitted via the network backbone 120 between the host computer 102 and the lubrication analyzer 90. The communication link preferably adheres to the RS232C or DeviceNet standard for communicating command and parameter information. However, any communication link suitable for carrying out the present invention may be employed.

Figure 3:
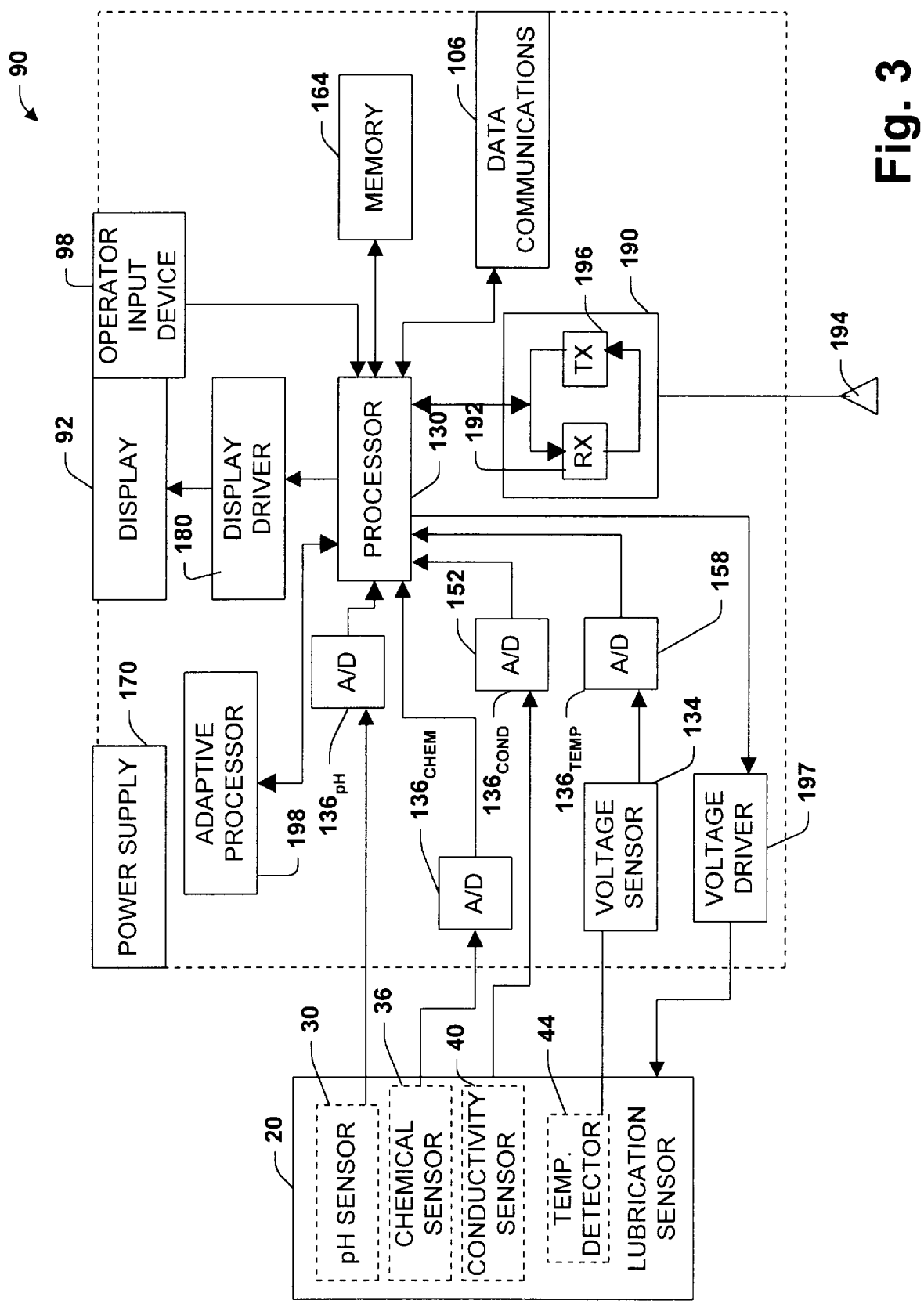
FIG. 3 is a block diagram of a lubrication sensor and lubrication analyzer in accordance with one embodiment of the present invention.

Referring now in particular to FIG. 3, a schematic representation of the present invention is shown according to one particular aspect of the present invention, wherein the lubrication analyzer 90 is integrated with the lubrication sensor 20. However, it will be appreciated from the discussion herein that the lubrication analyzer 90 may be located remotely from the motor 70. Furthermore, it is to be appreciated that the host computer may serve to carry out substantially all of the functions described herein performed by the lubrication analyzer 90. It is also to be appreciated that in accordance with another specific aspect of the present invention, the lubrication analyzer 90 (absent certain components) may be integrated onto a semiconductor chip with the lubrication sensor 20. In accordance with another specific embodiment, the lubrication analyzer 90 may be completely integrated within the motor 70 (e.g., in an intelligent motor), a gear box, or a bearing, for example.

In the preferred embodiment, the lubrication analyzer 90 includes a housing which is suitably shielded to protect the lubrication analyzer 90 from whatever environment (e.g., dust, moisture, heat, vibration, lubrication) the motor 70 is working in. Additionally, the interior of the lubrication analyzer 90 may be suitably insulated with thermal insulation between the motor and the lubrication analyzer so as to protect it from heat generated by the motor 70.

The lubrication sensor 20 includes the pH sensor 30, the chemical sensor 36, the conductivity sensor 40 and the temperature sensor 44. Each of the sensors 26 is operatively coupled to a processor 130 of the lubrication analyzer 90 via respective analog to digital (A/D) converters 136 which convert the analog signals output from the sensors 26 to digital form for processing by the processor 130.

The temperature detector 44 varies in electrical conductivity depending on the temperature of the lubricant. Accordingly, the temperature of the lubricant can be determined from the output of a voltage sensor 134 which is coupled to the temperature detector 44 because the output voltage will vary in correspondence with the lubricant temperature. The following table illustrates the analytic relationship between lubricant viscosity and lubricant temperature, which can be monitored via the conductivity of the temperature detector 44.

| CONDUCTIVITY OF TEMP. DETECTOR 40 | LUBRICANT TEMPERATURE | GOOD LUBRICANT VISCOSITY |
|---|---|---|
| $V_1$ | $T_1$ | $LV_1$ |
| $V_2$ | $T_2$ | $LV_2$ |
| $V_3$ | $T_3$ | $LV_3$ |
| . | . | . |
| . | . | . |
| . | . | . |
| $V_N$ | $T_N$ | $LV_N$ |

A more detailed discussion relating to the analytic relationship between lubricant viscosity and lubricant temperature is presented in co-pending U.S. patent application Ser. No. 09/054,117, entitled MICRO-VISCOSITY SENSOR AND LUBRICATION ANALYSIS SYSTEM EMPLOYING THE SAME, which is hereby incorporated by reference in its entirety.

The lubrication sensor 20 may be tailored to output measurements in any suitable format in accordance with the present invention. For example, the output signals may be provided as digital serial; digital parallel; or current (4–20 mA).

The processor 130 is responsible for controlling the general operation of the lubrication analyzer 90. The processor 130 is programmed to control and to operate the various components of the lubrication analyzer 90 in order to carry out the various functions described herein. The processor or CPU 130 can be any of a plurality of suitable processors, such as the p24T, Pentium 50/75, Pentium 60/90, and Pentium 66/100, Pentium PRO and Pentium 2, and other similar and compatible processors. The manner in which the processor 130 can be programmed to carry out the functions relating to the present invention will be readily apparent to those having ordinary skill in the art based on the description provided herein and thus further discussion related thereto is omitted for sake of brevity.

A memory 164 operatively coupled to the processor 130 is also included in the lubrication analyzer 90 and serves to store program code executed by the processor 130 for carrying out operating functions of the lubricant analyzer 90 as described herein. The memory 164 also serves as a storage medium for storing information such as nominal lubricant temperature, pH, electrochemistry, viscosity data, etc. The memory 164 may also include machine specific data and acceptable error bounds/deviation values which may be used to facilitate determining the suitability of the lubricant being analyzed. Furthermore, the memory 164 may be used to store current and historical lubricant or fluid parameter data, and corrective action which may be recommended. The data may be transmitted to a central processor and/or employed to perform time-based trending and analysis to determine lubricant or fluid health and future health and desirable re-lubrication interval.

The memory 164 includes read only memory (ROM) and random access memory (RAM). The ROM contains among other code the Basic Input-Output System (BIOS) which controls the basic hardware operations of the lubrication analyzer 90. The RAM is the main memory into which the operating system and application programs are loaded. The memory 164 is adapted to store a complete set of the information to be displayed. According to a preferred embodiment, the memory 164 has sufficient capacity to store multiple sets of information, and the processor 130 could include a program for alternating or cycling between various sets of display information. This feature enables the display 92 to show a variety of effects conducive for quickly conveying lubricant state information to a user.

Power is provided to the processor 130 and other components forming the lubricant analyzer 90 from a power supply 170.

The lubricant analyzer 90 includes a data communication system which includes a data communication port 106 and communications card (not shown), which is employed to interface the processor 130 with the host computer 102 via the network 120 (FIG. 2). The communication link preferably adheres to the RS232C or DeviceNet standard for communicating command and parameter information. However, any communication link suitable for carrying out the present invention may be employed.

It should be appreciated that the present invention may be used in a system which does not include the host computer 102. All processing including data analyses and lubricant or fluid state estimation and health determination could be accomplished by the processor 130 and the results transmitted to a PC or a control computer such as a programmable logic controller (PLC) (not shown) or only displayed locally on the lubricant analyzer display screen 92. Furthermore, only one data link may be required. According to another embodiment, the processor 130 could be employed to simply trigger a single bit, digital output which may be used to open a relay and turn the motor 70 off or signal an alarm.

The display 92 is coupled to the processor 130 via a display driver circuit 180 as is conventional. The display 92 may be a liquid crystal display (LCD) or the like. In the preferred embodiment, the display 92 is a fine pitch liquid crystal display operated as a standard CGA display. The display 92 functions to display data or other information relating to the state of the lubricant and if desired the state of the motor 70 and recommend action (e.g. change lube in 2 weeks). For example, the display 92 may display a set of discrete lubricant or fluid condition indicia such as, for example, temperature, pH, electrochemistry, viscosity, and normal operation indicia which is displayed to the operator and may be transmitted over the network 120. The display 92 is capable of displaying both alphanumeric and graphical characters.

Alternatively, the display 92 may comprise one or more light emitting diodes (LEDs) (e.g., a tri-state LED displaying green, yellow or red colors depending on the health state of the lubricant).

The lubrication analyzer 90 may also include its own RF section 190 connected to the processor 130. The RF section 190 includes an RF receiver 192 which receives RF transmissions from the host computer 102 for example via an antenna 194 and demodulates the signal to obtain digital information modulated therein. The RF section 190 also includes an RF transmitter 196 for transmitting information via a wireless link to the host computer 102 for example in response to an operator input. This wireless link may eliminate the cost, noise problems and other problems related with the wireline link 120.

The lubrication analyzer 90 includes a voltage driver 197 which is operatively coupled to the processor 130 and the lubrication sensor 20. The voltage driver 197 provides a series of desired voltage to the lubrication sensor 20 in order to drive certain sensing devices (e.g., chemical sensor 36).

The lubricant analyzer 90 may also include an adaptive processor 198 such as for example a neural network and/or an expert system to facilitate analyzing the health state of the lubricant. Alternatively, the adaptive processor 198 may be located in the host computer 102 if desired.

The programming or training of neural networks involves supplying the input and corresponding output data of samples containing features, similar to those being searched for. The neural network in turn learns by adjusting weights assigned to each of the neurons. The weights and threshold values of neurons of the neural network determine the propagation of data through the network and thus provides a desired output based on a respective set of inputs.

Expert systems are knowledge-based systems which are typically rule-based. An expert system is employed in accordance with the present invention by establishing a hardware or software based program which contains encoded domain knowledge from a knowledge expert as to the relationship between items of information being sought for classification—in this case lubricant state. That is, the expert system codifies expert knowledge as a rule or set of rules for each decision and stores given rules and data into the knowledge base. The expert system will typically employ an "inference" engine to derive health-related knowledge about the subject.

Once the processor 130 has processed all of the respective lubricant data, the processed data may be sent to the host computer 102 for subsequent analysis and trending. The host computer 102 may then make determinations as to the health of the lubricant based on the data received from the lubrication analyzer 90. As will be discussed in greater detail below in connection with FIG. 4*a*, the processor 130 may perform data fusion of the various sensed lubricant or fluid sensed parameter data to facilitate condensing, combining, evaluating and interpreting the various sensed data. Accordingly, lubricant maintenance can be scheduled to correspond with the state of the lubricant. Additionally, the processed data can be compiled for trend analysis and forecasting. Since the lubrication analyzer 90 is integrated with the motor 70, the data sampling rate can be substantially high thus providing for improved highly accurate and up to date data relating to the health of the lubricant.

However, as mentioned above, it is to be appreciated that lubricant diagnosis, trend analysis, forecasting, etc. that could be performed by the host computer 102 may also be performed directly by the lubrication analyzer 90.

Figure 4A:
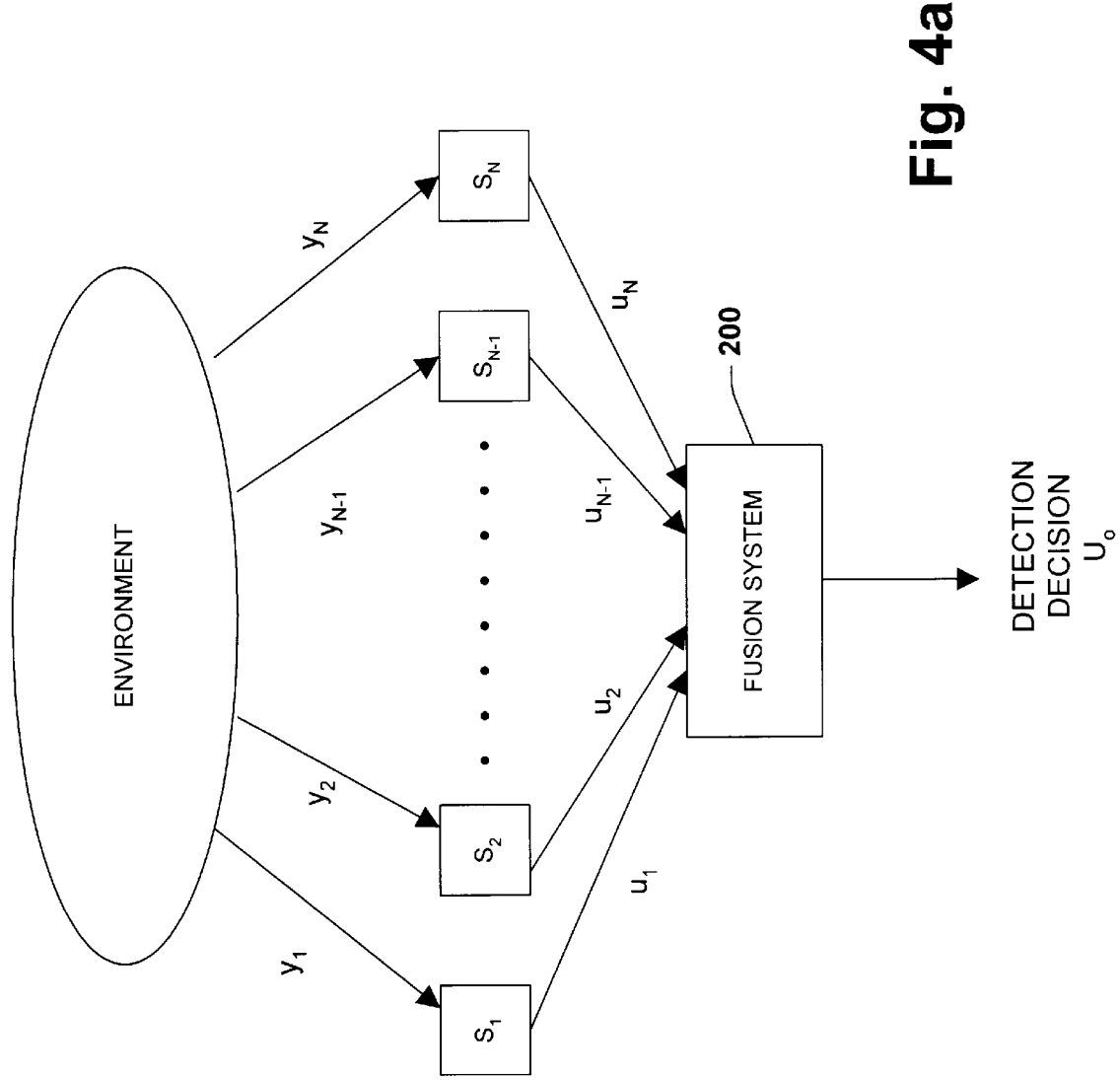
FIG. 4a is a function block diagram illustrating a data fusion process in accordance with one embodiment of the present invention.

Referring now to FIG. 4*a*, a data fusion process in accordance with the present invention is discussed. A common root cause of machinery failure is lubricant contamination by particles and moisture. In fact, failures often attributed to "normal wear" are the result of lubricant contamination. The inability of the lubricant to perform its intended function can result from high temperature operation or moisture, or the introduction of debris from the surrounding operating environment or from deterioration of internal machine components. Such undesirable operating condition should be identified quickly and reliably.

Most lubricant/fluid condition management activities fall into one of the following three categories: (1) lubricant/fluid health analysis; (2) system conditioning monitoring; and (3) wear or damage analysis. The first two categories relate to the role of the lubricant in providing protection for the machine components and also as a "local sensor" for system health monitoring. Suppliers of lubricants provide detailed technical information on the operating characteristics of their products. It is then the responsibility of the user to make sure that the lubricant has not degraded to the point where it is ineffective for the intended application. In this case, it is the condition of the lubricant that is being evaluated. Determining the condition of the lubricant requires inspection of the physical, chemical, and additive properties of the lubricant to determine if the lubricant is capable of performing its intended function. The lubricant properties that must be evaluated to assess the condition of the lubricating fluid are inherent to the lubricant and should be measurable from any representative sample of the lubricant.

Although the deterioration of the lubricating qualities of a lubricant can lead to machine operating problems which can escalate at an exponential rate, a lubricant whose physical, chemical, and additive properties are within expected tolerances is not by itself indicative of a healthy machine. The operating temperature of the lubricant, the level of contaminants in the lubricant, and the amount of moisture present in the lubricant are all relevant parameters for assessing the operation of the system. The analysis of a lubricant to determine the health of the system involves devising an appropriate sampling methodology, including the frequency and location of the samples that are to be taken. The present invention provides for a distributed collection of in situ multi-element sensor units, each capable of monitoring lubricant parameters such as temperature and contaminants—including debris particles and moisture, and can provide relevant information desirable for system health monitoring. More particularly, the lubrication sensor 20 of the present invention may include a plurality of different sensing devices such as for example, a temperature detector, pH sensor, viscosity sensor, electro-chemical sensor, electrical conductivity sensor, etc. One, several or all of such sensing devices 26 maybe situated on a single lubrication sensor chip and provide for in situ gathering of multiple lubricant parameters. Faults or failures in a bearing, for example, are often the result of excessive loading or the distribution of debris that induces contact between rotating elements. Before the contact can be detected using conventional vibration analysis, the cause (e.g., debris) or the effect (e.g., metal particulates in the lubricant or fluid) are often measurable in the lubricant or fluid. Furthermore, if these and other relevant measurements can be obtained within the operating environment of the device, e.g., the confines of the bearing, then mechanical faults as well as degradation in the lubricating fluid can be simultaneously diagnosed and localized. Moreover, the analysis may be performed in the context of a machinery-rolling element-lubrication system where each component mutually affects each other component.

The sensor system of the present invention includes sensors (transducers) 26 (FIG. 1) capable of measuring several different operating characteristics or parameters of the lubricant within the confines of the system (e.g., temperature, pH, conductivity, and viscosity (see FIGS. 5*a* and 5b)). Signal data from each of these transducers 26 is combined within a unified detection and decision framework to obtain useful information for both the condition of the lubricant and the process employing the lubricant.

An approach to formulate and solve this class of problems is often referred to as data fusion. Data fusion is the process of combining information from a set of distributed sensors, each of which is observing the same or similar/related features of the environment. It is well understood that the fundamental need for data fusion is because of the process of information fission that is inherent to in the process of sensing a physical environment through several different sensor modalities. Each sensor $(S_1-S_N)$ provides a unique window into the physical environment where the phenomena to be observed is occurring. Because the complete details of the phenomena being studied (e.g., detecting the operating state of the lubricant or fluid, or the process) are not contained within a single sensor window, there is information fragmentation or fission. These information fragments which are associated with the various sensor modalities can contain both independent and dependent components. The independent components are used to further fill out (or span) the information space and the dependent components are used in combination to improve the quality of common information because all sensor data is subject to error and noise. In this context, data fusion is the algorithmic processing of sensor data to compensate for the inherent fragmentation of information because the phenomena cannot be observed directly using a single sensor.

For example, in the application of multi-element sensor array data to determine the health of the lubricant or fluid, a combination of sensors (pH, temperature, conductivity, etc.) are employed, each sensor 26 providing information related to a particular aspect of the phenomena that is to be measured. This information is combined and analyzed in order to make a decision regarding the health of the lubricant or fluid. As sensor modalities are added and a number of multi-element sensor arrays distributed within the operating environment, a data fusion architecture provides the correct framework for condensing, combining, evaluating, and interpreting the available information in the context of the application.

There are a variety of different approaches to the problem of data fusion. The most common mathematical techniques are based on formulating the fusion problem in the context of detection and estimation as a statistical hypothesis testing problem (Neyman-Pearson) or as an optimization (Markov statistical decision) problem where the cost functional is either of the Bayesian risk type or of the entropy (mutual information) type. Other approaches which use pattern recognition, rule-based methods, and artificial neural networks and/or expert systems may be employed.

For the problem of detecting and diagnosing the degradation in the lubricant or fluid and condition-based monitoring of rotating machinery, the mathematical techniques are the most suitable. In this context, the sensed data is used to evaluate the validity of various hypotheses. For example, hypothesis $H_0$ is true if the condition of the lubricant is good; hypothesis $H_1$ is true if the operating condition of the rotating machine is good, other hypotheses $H_i$ where i=2, . . . n are defined according to various predetermined fault modes. The objective of the sensor fusion algorithm is to use the data from various sensor elements to determine which hypothesis (or several) is true (or most likely true). A probabilistic framework is most appropriate for computing and analyzing the various hypotheses. For example, consider a situation where a multi-element sensor array incorporates a temperature sensor $(y_1)$, a pH sensor $(y_2)$, and a conductivity sensor $(y_3)$, then the problem of determining if the lubricant or fluid is healthy is equivalent to computing the Probability $(H_0|y_1, y_2, \text{ and } y_3)$ in order to determine the overall operating state (e.g., health) of the system.

The data fusion architecture shown in FIG. 4a decomposes the computation of Probability $(H_0|y_1, y_2, y_3 \ldots y_N)$ into individual "local" decisions $(U_1, U_2, U_3, \ldots U_N)$ and these are combined in a fusion center 200 to compute Probability $(H_0|y_1, y_2, y_3 \ldots y_N)$ and the overall health of the system. In a decentralized parallel sensor architecture as shown in FIG. 4a the centralized fusion center 200 is used to combine the sensor data. Here each sensing device 26 (FIG.1) accepts data $(y_i)$ from the environment, locally processes this information and transfers this local information (or decision) $(u_i)$ to the fusion center 200 for further processing and decision making $(U_0)$.

Figure 4B:
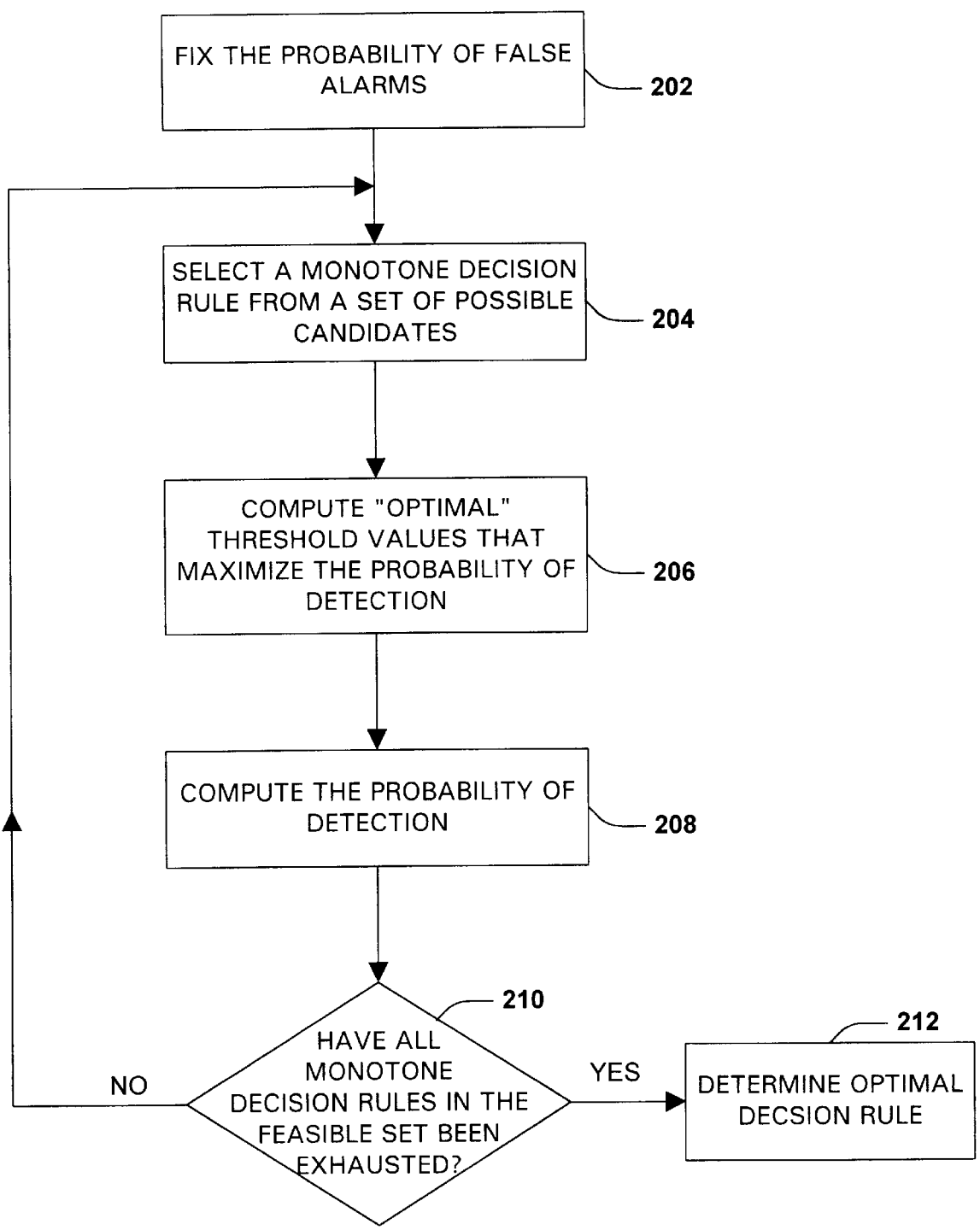
FIG. 4b is a flow diagram illustrating an algorithm for determining optimal decision rules in accordance with the present invention.

In the Neyman-Pearson framework, the design of both the local and global decision rules to achieve the detection decision $U_0$ is formulated as a constrained optimization problem where the objective is to maximize the probability of detection while constraining the probability of false alarms. It is well known that under the assumption of conditional independence (e.g., the sensed data are statistically independent conditioned on the hypothesis), the optimal local and global decision rules are of the threshold type in terms of the appropriate likelihood ratio. This is of course, the familiar likelihood ratio test (LRT) for hypothesis testing in a statistical decision theory framework. Since the optimal decision rule is a positive unate function, for sensor configurations such as the present invention, search algorithms like the one illustrated in FIG. 4b may be effectively utilized to find the optimal decision rules.

Initially, in step 202 the search algorithm sets or fixes the probability of a false alarm occurring. Next, in step 204, the algorithm selects a monotone decision rule from a set of possible candidates. For the rule selected in step 204, the algorithm in step 206 computes "optimal" threshold values that maximize decision probability. Next, in step 208 the probability of detection is computed for the selected decision rules. In step 210, the algorithm determines if all monotone decision rules in a feasible set have been exhausted. If no, the algorithm returns to step 204 to select another monotone decision rule from the feasible set. If yes (all monotone decision rules in the feasible set have been exhausted), the algorithm proceeds to step 212 where the optimal decision rule is determined, which is the decision rule that has the largest probability of detection.

The following discussion focuses on probabilistic computations to support the computation of lubricant health from on-line sensor data. Assume a sequence of sensor measurement, $y_i[k]$, where i denotes the sensor index and k denotes the time (sampling) index. Let $H_j$ denote the lubricant health hypothesis that is to be tested, for example, $H_0=\{$the lubricant is in good condition, $H_1=\{$viscosity of the lubricant is below value xxx$\}$, . . . The basic problem is to compute $P_j[k]=\text{Prob}\{H_j \text{ is true } |y_i[I], I=0, 1, \ldots k\}$. This can be interpreted as a decentralized nonlinear filtering problem because it is desired to build up this computation from decentralized (local) computations based on smaller subsets of the sensor data and update sequentially in time—hence, the need for data fusion. It is also possible to perform a centralized computation.

Data fusion techniques are well-known, and therefore further discussions related thereto are limited for sake of brevity. U.S. Pat. No. 5,661,666 entitled Constant False Probability Data Fusion System describes data fusion in substantial detail, and this patent is incorporated herein by reference in its entirety.

Thus, the present invention employs sensor fusion to combine information from two or more sensors in accordance with a pre-established model or framework so as to: (a) improve the accuracy of sensed information; (b) determine the state of a system using the combined sensed information (state estimation); and (c) derive new unmeasurable parameters of the system.

With respect to improving accuracy of sensed information, the following is one specific example. Lubricant conductivity may be measured by employing two electrodes and measuring resistance. However, the presence of water in the lubricant will affect the conductivity of the lubricant. If water concentration (p.p.m.) can be measured with another sensor and a certain standard conductivity value for water is assumed, the lubricant conductivity measure may be compensated by the standard conductivity value for water to obtain a more accurate reading of the lubricant conductivity. Alternatively, multiple conductivity sensors with different probe separation and differing tip to tip potential, respectively, may be combined to provide a more accurate measure of conductivity by combining these sensed values in an algorithmic manner.

However, in another embodiment a chemical/electrochemical model may be employed to determine if a serious lubricant condition exists (excessive oxidation) or inconsistent condition (e.g., extremely high viscosity unaccounted for or inconsistent with other sensor readings. Alternatively, sensor data may be combined using a model-free estimator to establish the state of the lubricant. For example, techniques such as unsupervised neural network schemes may be readily employed.

Regarding new parameter derivation, if it is desired to know metal particulate concentration and particle size ($m_c$), and $m_c$ cannot be measured directly, an approximate measure for $m_c$ may be computed and this value used in subsequent analysis with other measured (or computed values) to determine the health (or operating condition) of the lubricant. In this example, it is known that metal particles act as a catalyst for the oxidation of the lubricant. The rate of oxidation will be affected by the particulate concentration (among other factors). Other sensed lubricant parameters may also provide evidence of the concentration of metal particulates such that:

$$m_c = f(o_r, c, d, w_c, v, f_v)$$

where
 $o_r$=oxidation rate
 c=conductivity
 d=dielectric strength
 $w_c$=water content
 v=viscosity
 $f_v$=vibration energy at characteristic frequencies.

A model which incorporates the above measurable quantities is then used to derive a critical unmeasurable quantity (metal particulate concentration ($m_c$)). This parameter ($m_c$) is a parameter highly indicative of the health (operating condition) of the lubricant and/or system employing the lubricant. There may be no other manner in which to obtain the value for $m_c$ in situ, especially for larger size particulates (e.g., 10 $\mu$ and higher).

As another example, rather than using an explicit electrochemical model as above, a neural network 216 (see FIG. 4c) may, be trained to compute the new derived parameter. For example, as in the previous case multiple lubricant samples that span the range of particulate concentration may be extracted and sampled in a laboratory and direct measurements taken for all parameters including metal particulate concentration and size. These multiple samples may then be used to train the neural network 216 employing a supervised learning scheme such as a feed forward error back propagation scheme. The neural network derived parameter ($m_c$) may then be used in subsequent analysis as previously described.

In another embodiment of the present invention, the sensed lubricant parameters may be employed to generate Fourier Transform InfraRed (FTIR) or Attenuated Total Reflectance (ATR) spectra. Laboratory analysis of lubricants may include FTIR or ATR plot(s) to identify the composition of the lubricant with regard to characteristics such as water content, degree of oxidation, additives present, and contaminants. The present invention may be employed to synthesize the FTIR/ATR spectra from measured sensed parameters of the lubricant. The intensity values at select critical frequencies corresponds to the IR absorption of certain components at these frequencies which in turn may be proportional to the concentration of the specified component. The absorption of the IR energy is related to the concentration levels according to the Beer-Lambert Law:

$$A = K \cdot b \cdot C$$

where
 A=absorbency of a sample (at a frequency);
 K=absorptivity of the component;
 b=unit of thickness;
 C=concentration of the component.

The FTIR/ATR intensity values may be generated using regression techniques to fit an analytical relationship:

$$A = f(s_1, s_2, s_3, \ldots s_n)$$

where the absorption at a particular frequency is a function of "n" sensed parameters—"n" being an integer. Alternatively, A, the absorption intensity at critical frequencies could be generated using the aforementioned neural network technique with supervised learning.

Another embodiment of the present invention may provide for synthesizing (such as with the neural network 216) a new parameter which may directly indicate the health (operating condition) of the lubricant or fluid. For example, the present invention may be employed to synthesize the ratio of sulfates plus carboxyls divided by water content. Such a parameter may indicate the likelihood of the lubricant to begin corroding a bearing surface, for example.

Figure 4D:
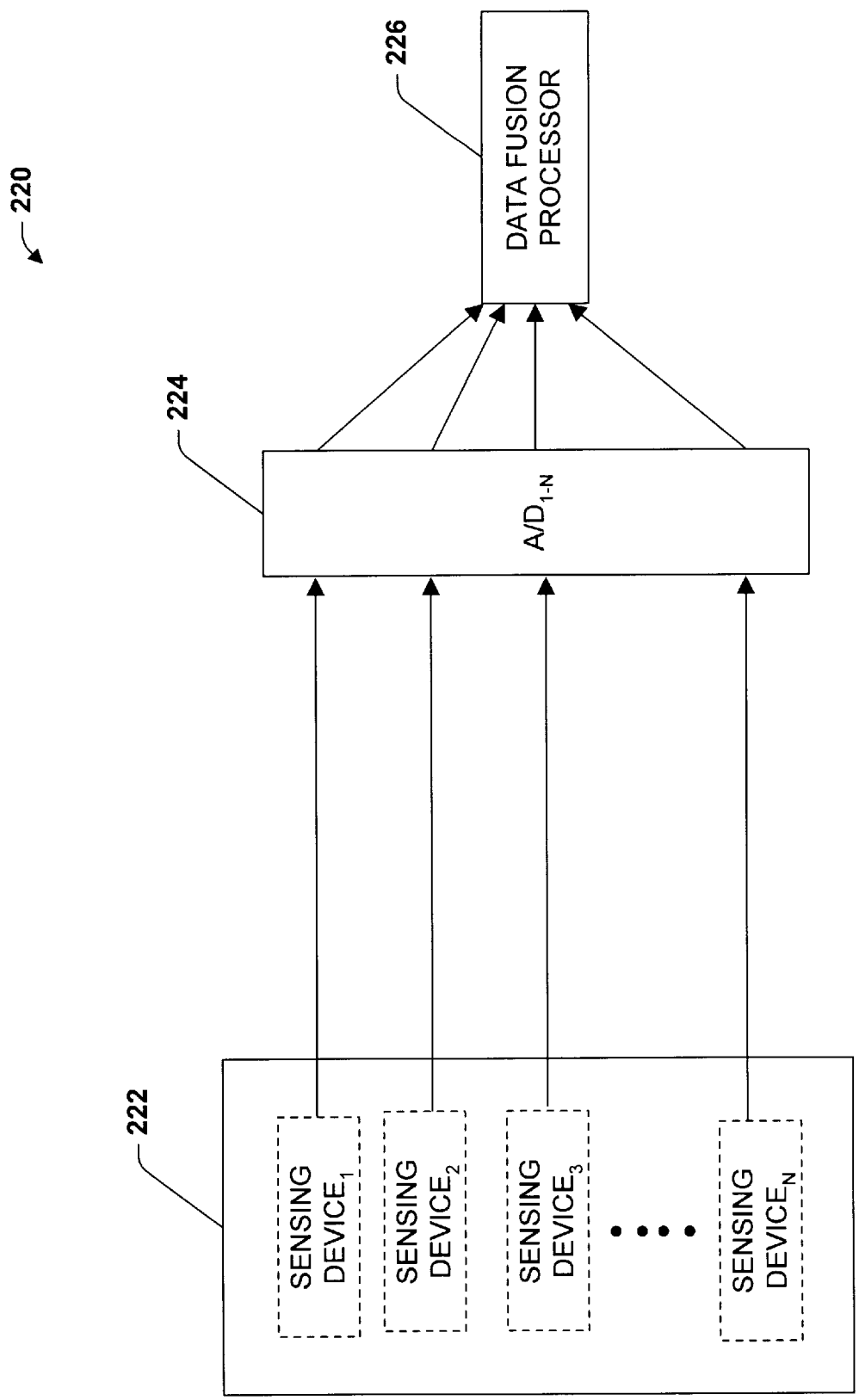
FIG. 4d is a block diagram of a plurality of sensing devices operatively coupled to a data fusion processor in accordance with the present invention.

Turning now to FIG. 4d, a schematic block diagram of a data fusion system 220 in accordance with one embodiment of the present invention is shown. The data fusion system 220 includes a multi-device sensing system 222, which includes a plurality of sensing devices (1-N). Each sensing device provides for sensing various parameters of a lubricant or fluid being analyzed. The sensed parameters from the sensing devices of the multi-device sensing system 222 are input into an analog to digital conversion system 224 which converts the analog values from the various sensing devices into digital form for processing by a data fusion processor 226. The data fusion processor 226 employs a data fusion framework on the digitized sensed parameters in the manner described above to provide for facilitating condensing, combining, evaluating and interpreting the various sensed data in order to facilitate rendering a health (operating condition) assessment of the lubricant or fluid being analyzed.

Figure 4E:
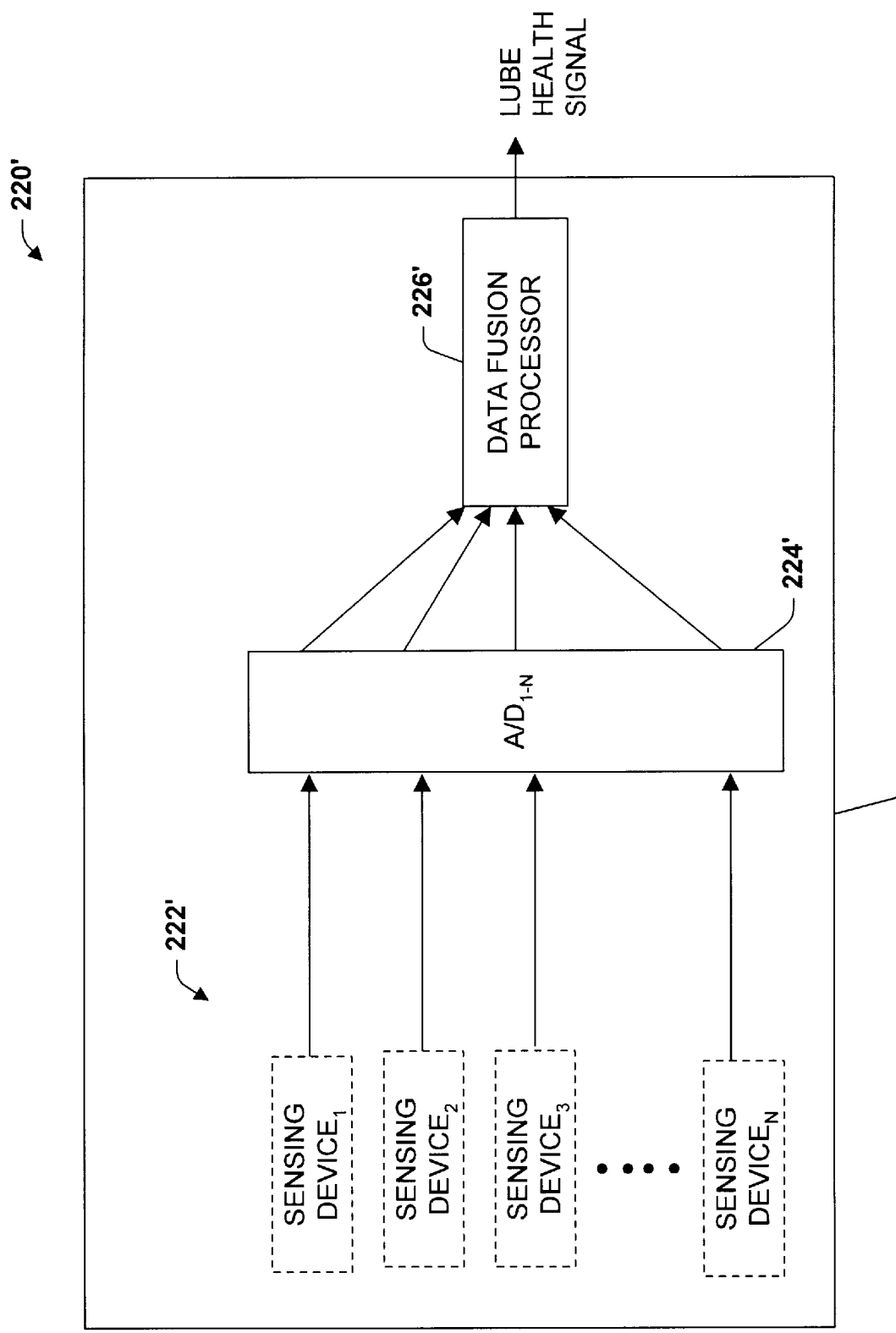
FIG. 4e is a block diagram of a lubrication analyzer including a plurality of sensing devices and a data fusion processor on a single semiconductor base in accordance with the present invention.

FIG. 4e is another embodiment of the present invention similar to the embodiment of FIG. 4d. Like components between FIG. 4d and FIG. 4e include like reference numerals except that the reference numerals of FIG. 4e are also followed by a prime ('). In this embodiment, the sensing devices 222', the analog to digital conversion system 224' and the data fusion processor 226' are all integrated onto a single semiconductor surface 230.

Each sensing device of FIGS. 4d and 4e may comprise a pH sensor or a temperature sensor or a electrical conductivity sensor or a viscosity sensor or a chemical sensor, or a combination thereof. Thus, some sensing devices may be only a single parameter sensor while other sensing devices may be a complete lubrication sensor (including a plurality of sensors for sensing different parameters).

Figure 5A:
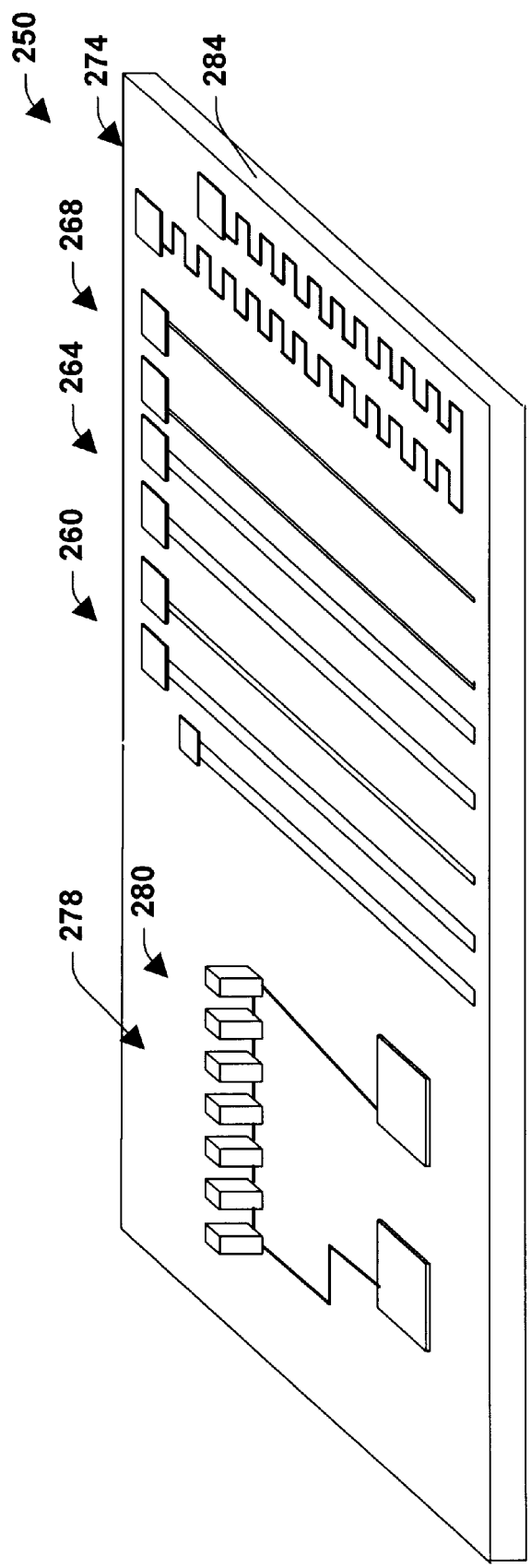
FIG. 5a is a perspective illustration of a lubrication sensor in accordance with another embodiment of the present invention.

FIG. 5a illustrates yet another embodiment of the present invention. In this embodiment a multi-element sensor 250 is provided which includes a pH sensor 260, an electrochemical sensor 264, a electrical conductivity sensor 268, a temperature sensor 274, and a viscosity sensor 278. The pH sensor 260, the electrochemical sensor 264, the conductivity sensor 268, and the temperature sensor 274 are essentially the same as that described in connection with FIG. 1 and therefore further discussion related thereto is omitted for sake of brevity. The viscosity sensor 278 provides for sensing the viscosity of the lubricant or fluid being analyzed. In short, the viscosity sensor 278 works in conjunction with the temperature sensor 274 to facilitate analyzing the viscosity of the lubricant or fluid being analyzed.

The viscosity sensor 278 includes a plurality (e.g., array) of finger-like elements (e.g., cilia) 280 which are plated with an electrically conductive material. The finger-like elements 280 extend perpendicularly from a surface 284 of the sensor, and the sensor 278 functions based on the phenomena that a dissipative or damping force that resists the motion of the energized finger-like elements 280 results in an increased power demand to maintain oscillation of the finger-like elements 280 at a particular frequency. A lubricant or fluid of high viscosity will exert a greater damping force on the oscillating finger-like elements 280 than a lubricant of lower viscosity. As a result, more power is required to maintain oscillation of the finger-like elements 280 at a particular frequency in a high viscosity lubricant or fluid than a lubricant or fluid of lower viscosity. Thus, the viscosity of a lubricant or fluid may be determined via the micro viscosity sensor 278 of the present invention by monitoring the power required to oscillate the finger-like elements 280 at a particular frequency and/or range of frequencies. Since the viscosity of a lubricant or fluid is also a function of lubricant or fluid temperature (e.g., typically, the higher the lubricant or fluid temperature the lower the lubricant or fluid viscosity), the present invention also employs the temperature detector 274 to correlate the temperature of the lubricant or fluid with the aforementioned power requirements to accurately interpret lubricant or fluid viscosity. A more detailed discussion relating to the operation and fabrication of such a viscosity sensor is found in U.S. patent application Ser. No. 09/054,117, entitled MICRO-VISCOSITY SENSOR AND LUBRICATION ANALYSIS SYSTEM EMPLOYING THE SAME, which as mentioned above is hereby incorporated by reference in its entirety.

Figure 5B:
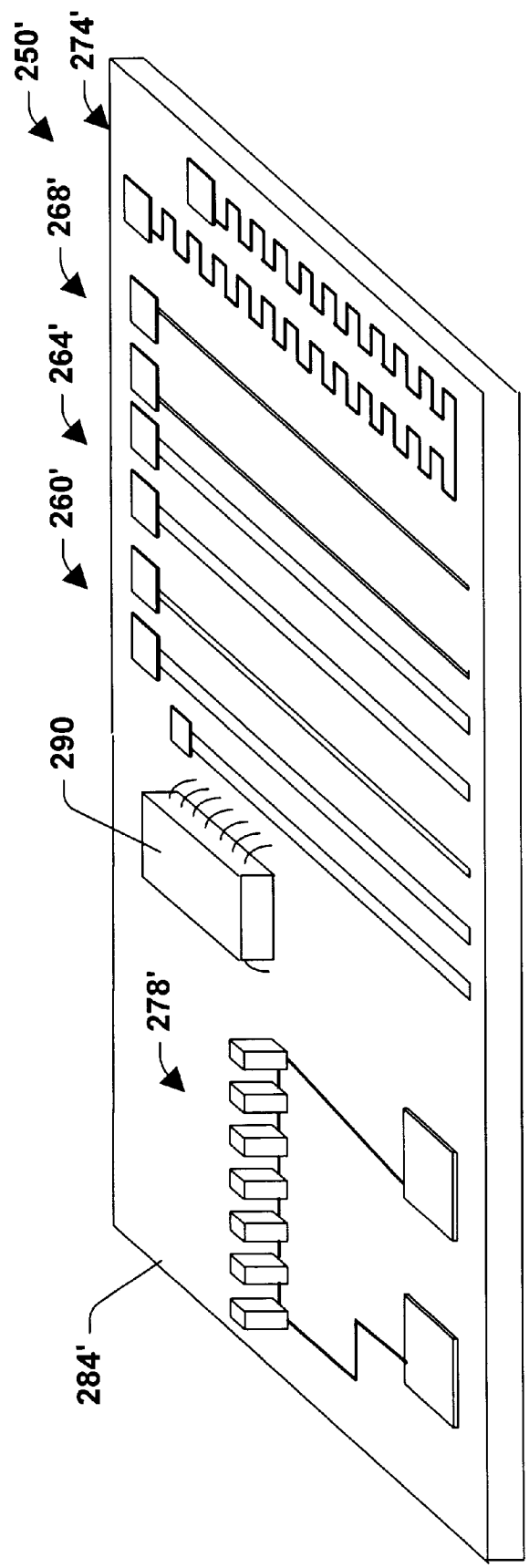
FIG. 5b is a perspective illustration of a lubrication sensor in accordance with yet another embodiment of the present invention.

FIG. 5b illustrates another embodiment of the present invention similar to the embodiment of FIG. 5a. Like components between FIG. 5a and FIG. 5b include like reference numerals except that the reference numerals of FIG. 5b are also followed by a prime ('). In this embodiment, the multi-element sensing system 250' also includes a processor 290 integrated on the semiconductor surface 284'. The processor 290 provides for carrying out the general operations of the system 250' including data fusion in accordance with the data fusion framework described above. The processor 290 can be any of a plurality of suitable processors, such as for example: CPU die or processor/logic/storage bonded (flip chip) to the sensor substrate—the sensor elements may be wire bonded to processor I/O connection points. The manner in which the processor 290 can be programmed to carry out the functions relating to the present invention will be readily apparent to those having ordinary skill in the art based on the description provided herein and thus further discussion related thereto is omitted for sake of brevity.

Thus, this embodiment provides for a substantially autonomous lubricant analysis system. The system 250' may provide for performing lube analyzer functions as well as affording for self diagnosis. The system 250' may also be able to verify that it is in a feasible operating regime.

Turning now to FIG. 6a, a lubricant analysis system 350 in accordance with an embodiment of the present invention is shown. In this embodiment, it is desired to monitor the state of a lubricant 356 employed to lubricate a motor bearing 358. As shown, a multi-element sensor 360 (FIGS. 1, 5a, 5b) is located proximate to the motor bearing 358 and is in contact with the bearing lubricant 356. The multi-element sensor 360 is also operatively coupled to a lubricant analyzer 370 which receives and processes data gathered by the multi-element sensor 360 in the manner described above. The lubricant analyzer 370 includes a data fusion system 372 for performing the data fusion of sensed parameters in accordance with the present invention.

In many motor designs, and particularly in motor designs utilizing spherical or self-aligning bearings, the use of unsuitable lubrication (degraded, contaminated, etc.) prevents maintaining a suitable lubrication film between the bearing and the bearing raceway so as to minimize wear and heating of the bearing. In turn, this inadequate lubrication oftentimes results in excessive friction, wear, and heat, which in turn may cause premature failure of the bearing thus possibly resulting in detrimental effects on the health and efficiency of the motor.

The present invention affords for monitoring the health of the bearing lubricant in a precise, reliable, inexpensive, convenient and substantially continuous manner. The lubricant analysis system 350 provides for frequently monitoring the health state of the lubricant 356, and can provide for scheduled maintenance of the lubricant 356 in order to facilitate maximizing the life and efficiency of the motor bearing 358 and minimizing maintenance cost.

It is to be appreciated that the present invention has numerous applications (e.g., forced lubrication systems; gear boxes; hydrodynamic bearings and other bearing systems, oils, grease, hydraulic fluids, cutting oils and other types of fluids where measured and derived knowledge thereof is desired). Each such fluid is susceptible to problems and exhibit symptoms with viscosity and temperature as described here (e.g. contamination, breakdown). All such applications are intended to fall within the scope of the present invention as defined in the claims.

FIG. 6b illustrates another aspect of the present invention wherein the lubricant analyzer 370 is coupled to two different multi-element sensors $360_a$ and $360_b$. Multi-element sensor $360_a$ is coupled to a load end bearing $358_a$, and multi-element sensor $360_b$ is coupled to a fan end bearing $358_b$. The lubricant analyzer 370 will monitor the health states of lubricants $356_a$ and $356_b$ for each respective bearing.

It is to be appreciated that a plurality of multi-element sensors ($360_1$ thru $360_n$) may be coupled to a single lubricant analyzer 370 as shown in FIG. 6c. Thus, the health state of lubricants of several different pieces of equipment (e.g., motors, gear box, pillow block, pump) may be monitored by the single lubricant analyzer 370.

FIGS. 7a–7f illustrate various environments in which the multi-element sensor 20, 250, 250' of the present invention may be employed. It is to be appreciated that these environments are only some example environments of many and that the present invention is not intended to be limited to only the environments described herein.

Figure 7A:
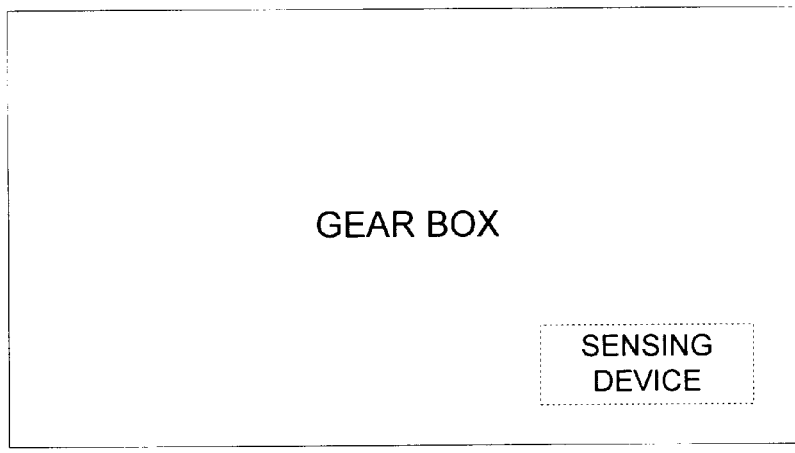
FIG. 7a is a schematic block diagram of a lubrication sensor sensing device being employed in connection with a gear box in accordance with the present invention.

FIG. 7a is a schematic block diagram illustrating the multi-element sensing device 20, 250, 250' being employed in connection with analyzing lubricant or fluid used in a gear box 400.

Figure 7B:
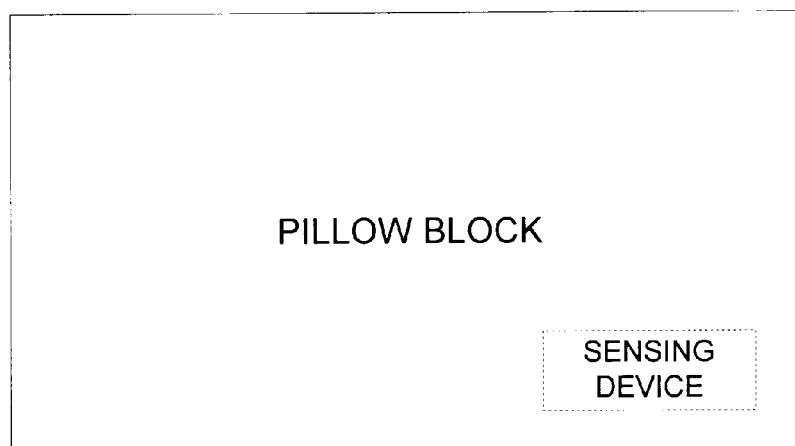
FIG. 7b is a schematic block diagram of a lubrication sensor sensing device being employed in connection with bearings for a pillow block in accordance with the present invention.

FIG. 7b is a schematic block diagram illustrating the multi-element sensing device 20, 250, 250' being employed in connection with analyzing lubricant or fluid used in a bearing set in a pillow block 402.

Figure 7C:
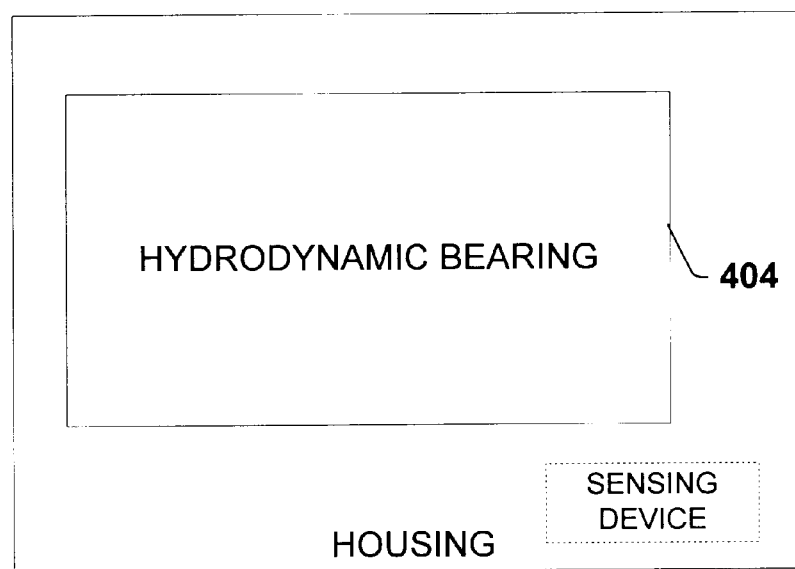
FIG. 7c is a schematic block diagram of a fluid sensing device being employed in connection with a hydrodynamic bearing in accordance with the present invention.

FIG. 7c is a schematic block diagram illustrating the multi-element sensing device 20, 250, 250' being employed in connection with analyzing lubricant or fluid used in a hydrodynamic bearing 404 housed in housing 406.

Figure 7D:
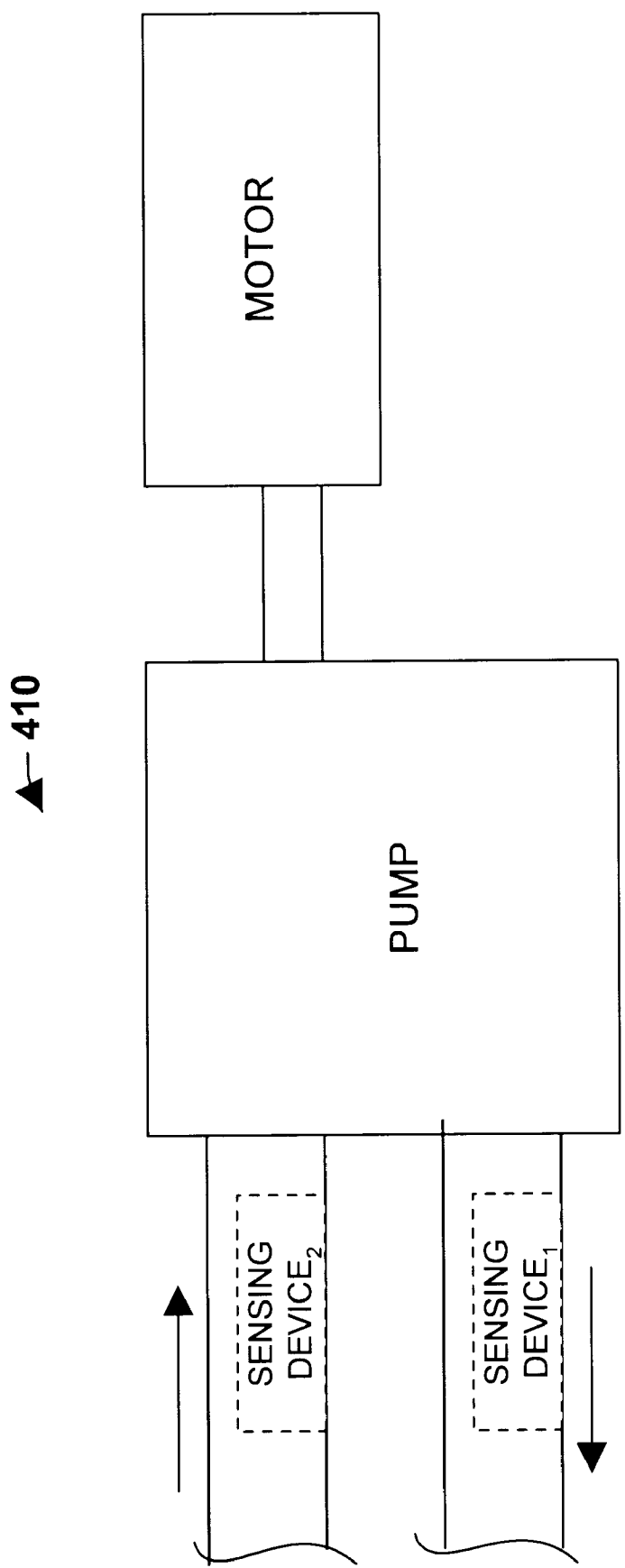
FIG. 7d is a schematic block diagram of a hydraulic fluid sensing device being employed in connection with a hydraulic pump and motor in accordance with the present invention.

FIG. 7d is a schematic block diagram illustrating several multi-element sensing devices 20, 250, 250' being employed in connection with a pump system 410, wherein one sensing device senses parameters relating to fluid or lubricant exiting the pump and the other sensing device senses parameters relating to fluid or lubricant entering the pump.

Figure 7E:
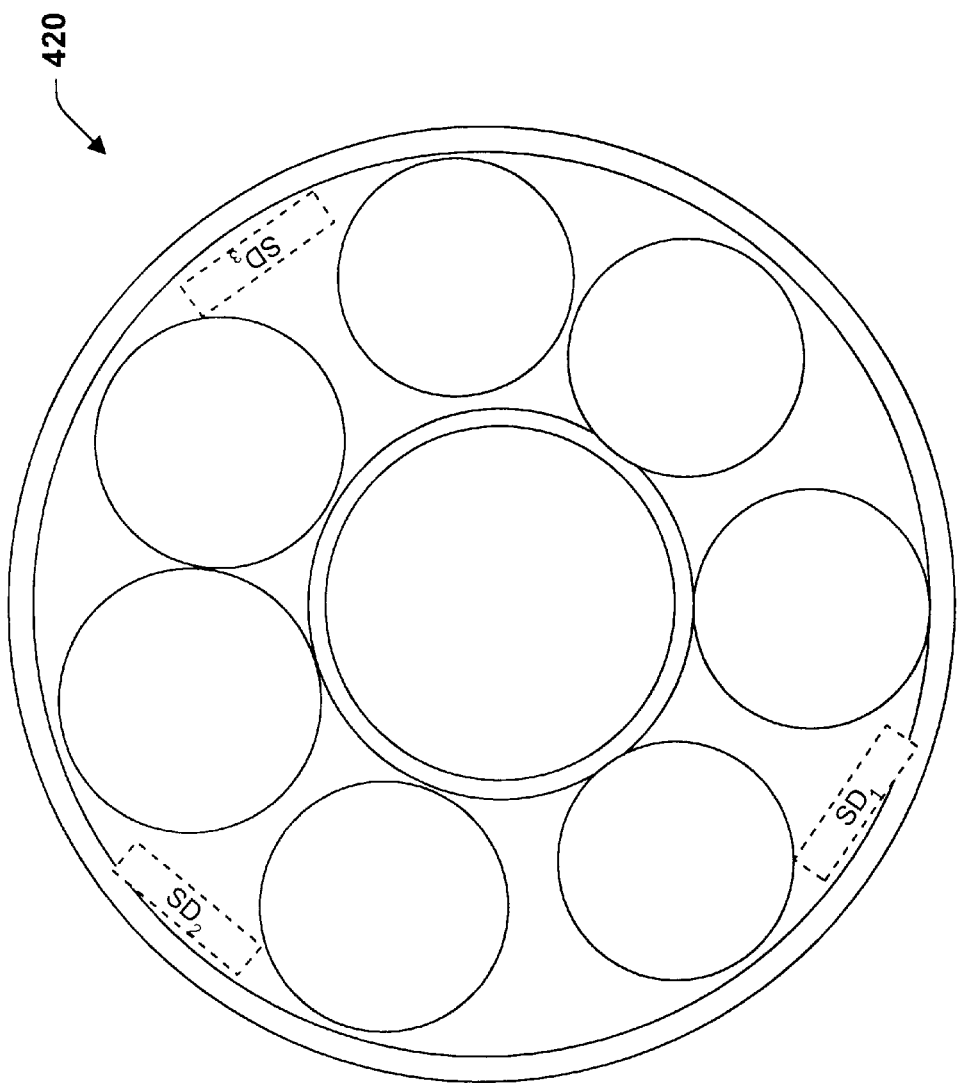
FIG. 7e is a schematic block diagram of a plurality of lubrication sensing being employed in connection with a motor bearing in accordance with the present invention.

FIG. 7e is a schematic block diagram illustrating several multi-element sensing devices 20, 250, 250' being employed in connection with a bearing 420, wherein the sensing devices are suitably positioned along the bearing raceway to sense parameters relating to lubrication of the bearings.

Figure 7F:
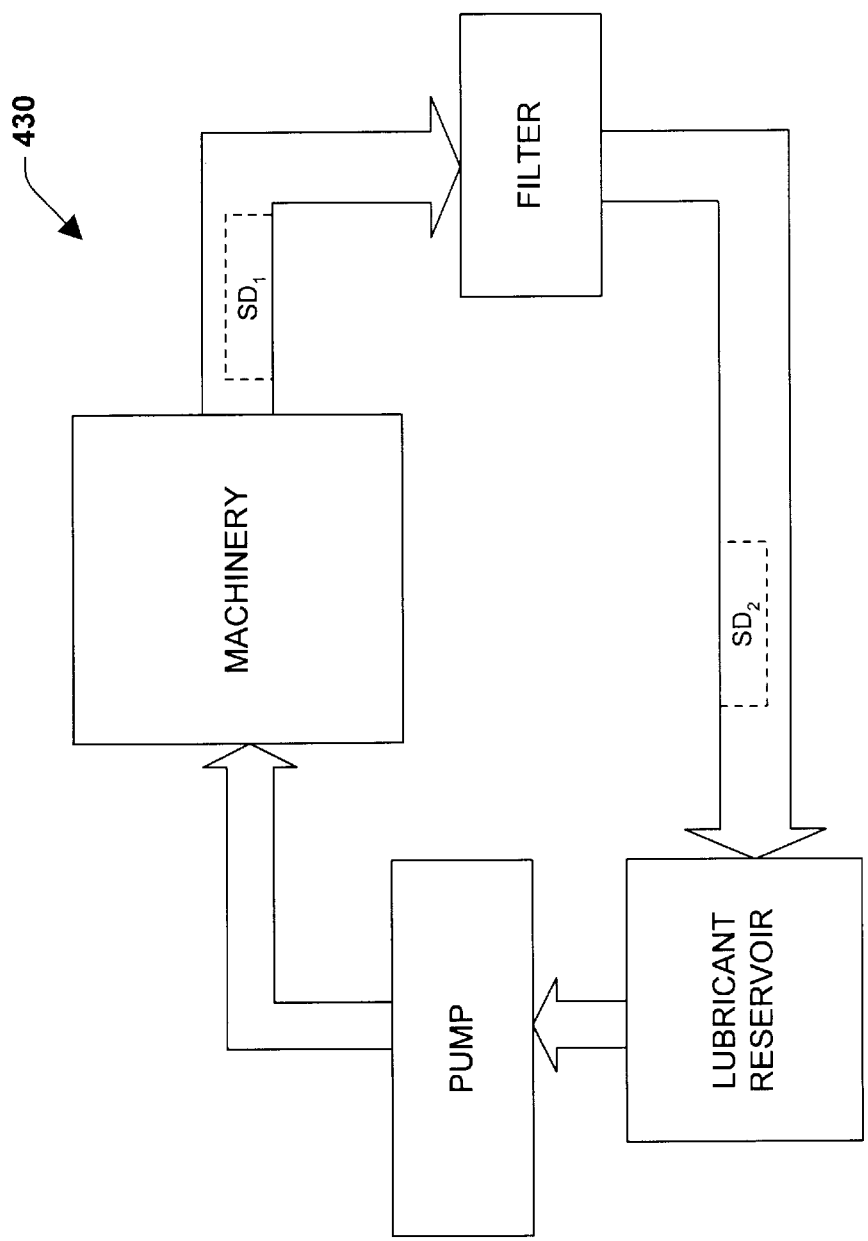
FIG. 7f is a schematic block diagram of a set of lubrication sensors being employed in connection with a machinery lubrication system in accordance with the present invention.

FIG. 7f is a schematic diagram illustrating a couple of multi-element sensing devices 20, 250, 250' being employed in connection with a process 430, wherein one sensing device senses parameters relating to fluid exiting a machine and the other sensing device senses parameters relating to fluid exiting a filter.

Turning now to FIGS. 8–15, an illustrative batch fabrication methodology for the lubricant sensor 20 of FIG. 1 is provided. Referring now to FIG. 8 in particular, the process begins with a substrate layer 500 of semiconductor material such as silicon for example, but it is to be appreciated that any suitable material for carrying out the present invention may be employed. A plurality of different masking steps are performed on the substrate 500 to deposit the different metals which are employed in forming the various sensors 26.

Figure 10:
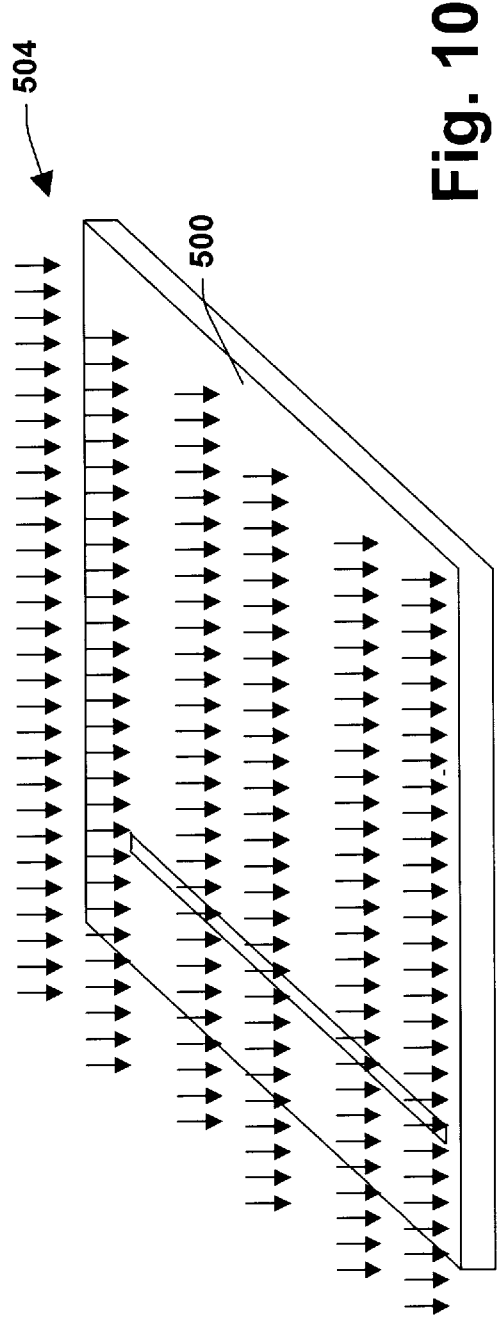
FIG. 10 is a perspective illustration of the substrate of FIG. 9 being masked, etched and patterned to form a pH reference electrode and chemical sensor in accordance with one embodiment of the present invention.
Figure 11:
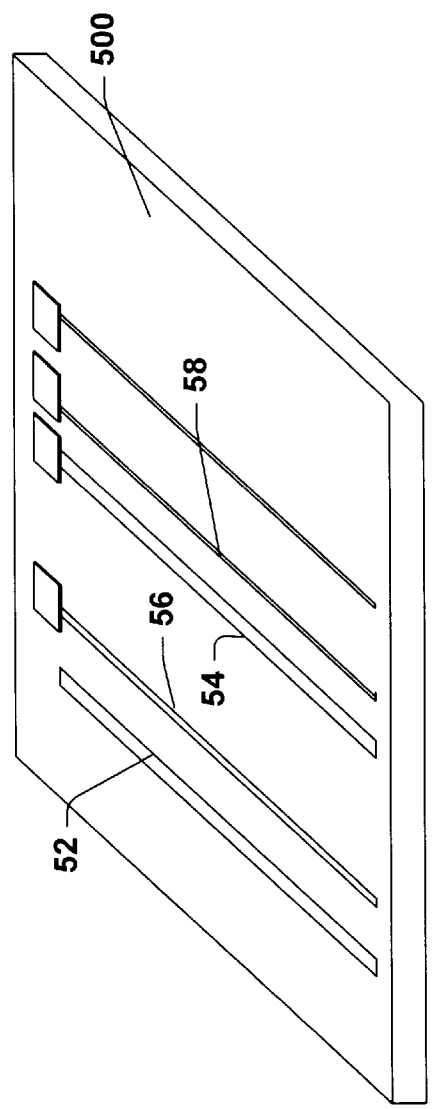
FIG. 11 is a perspective illustration of the substrate of FIG. 10 after formation of the pH reference electrode and electro-chemical sensor in accordance with the present invention.
Figure 12:
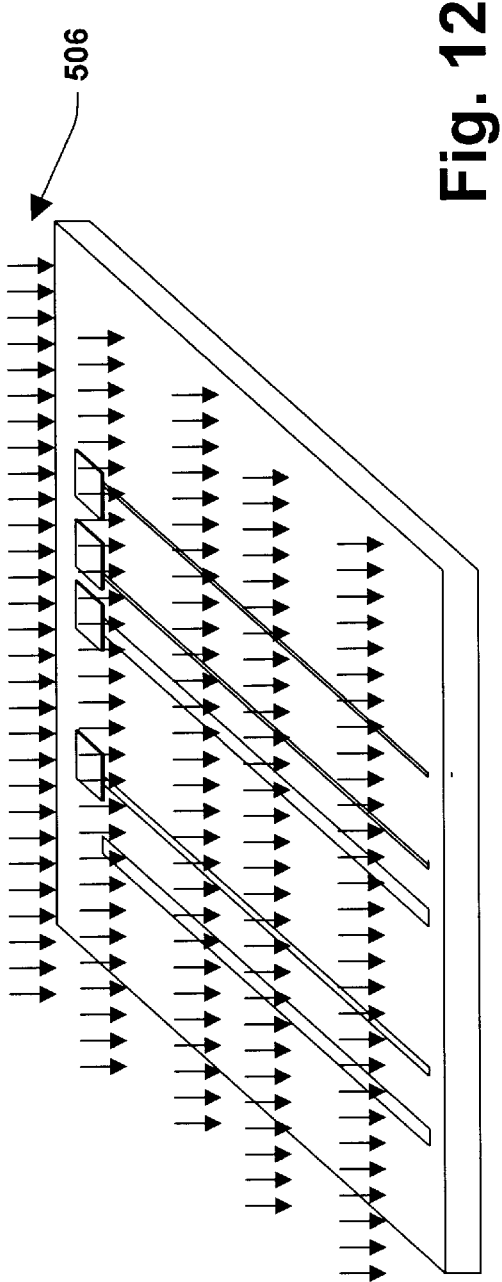
FIG. 12 is a perspective illustration of the substrate of FIG. 11 being masked, etched and patterned to form platinum contacts and a temperature sensor in accordance with the present invention.
Figure 13:
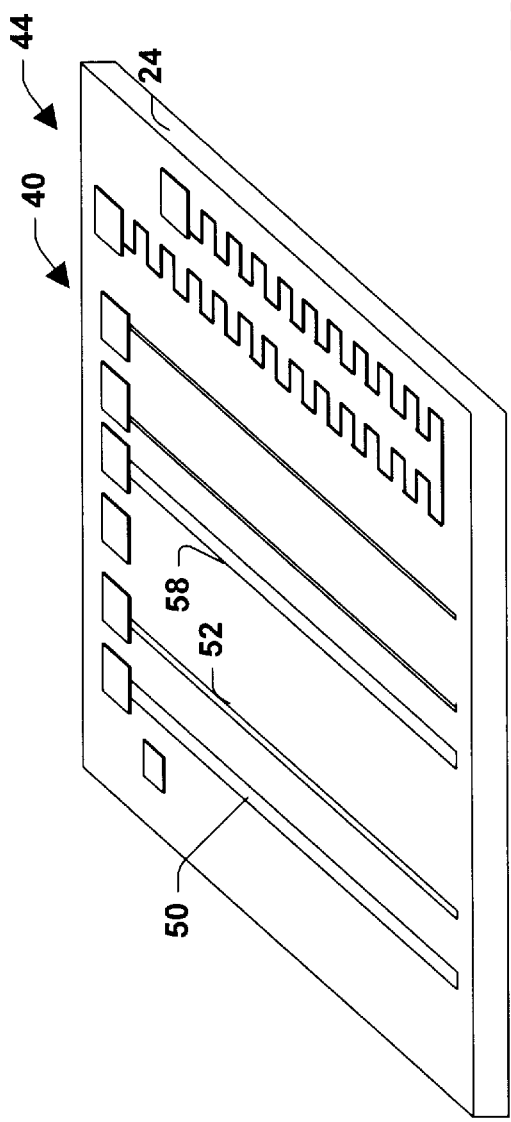
FIG. 13 is a perspective illustration of the substrate of FIG. 12 after formation of the platinum contacts and a temperature sensor in accordance with the present invention.
Figure 14:
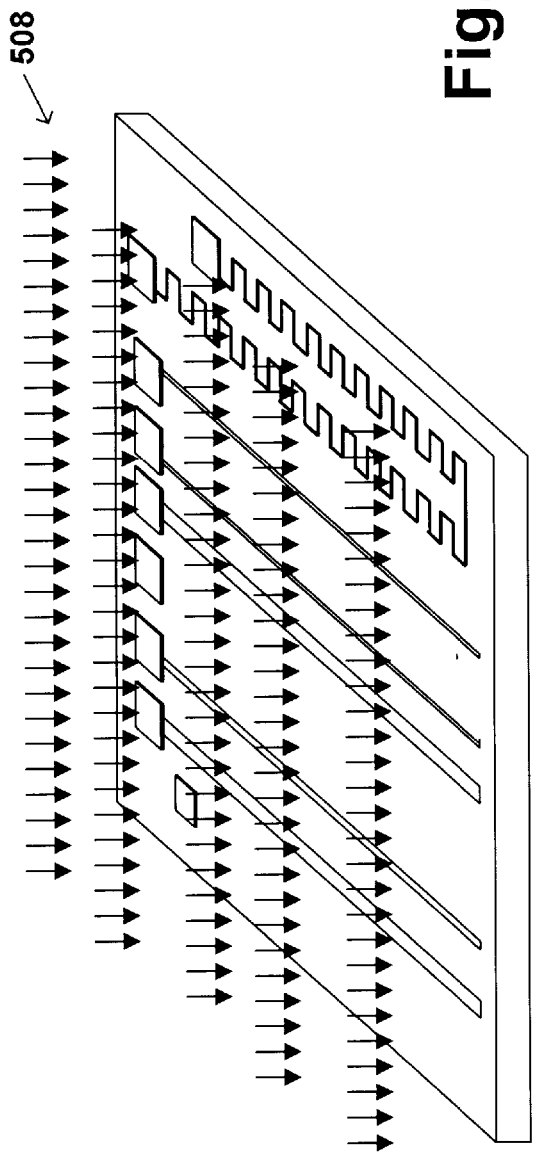
FIG. 14 is a perspective illustration of the substrate of FIG. 13 being masked, etched and patterned to form silver reference electrodes for a pH sensor and electrical conductivity sensor in accordance with the present invention.
Figure 15:
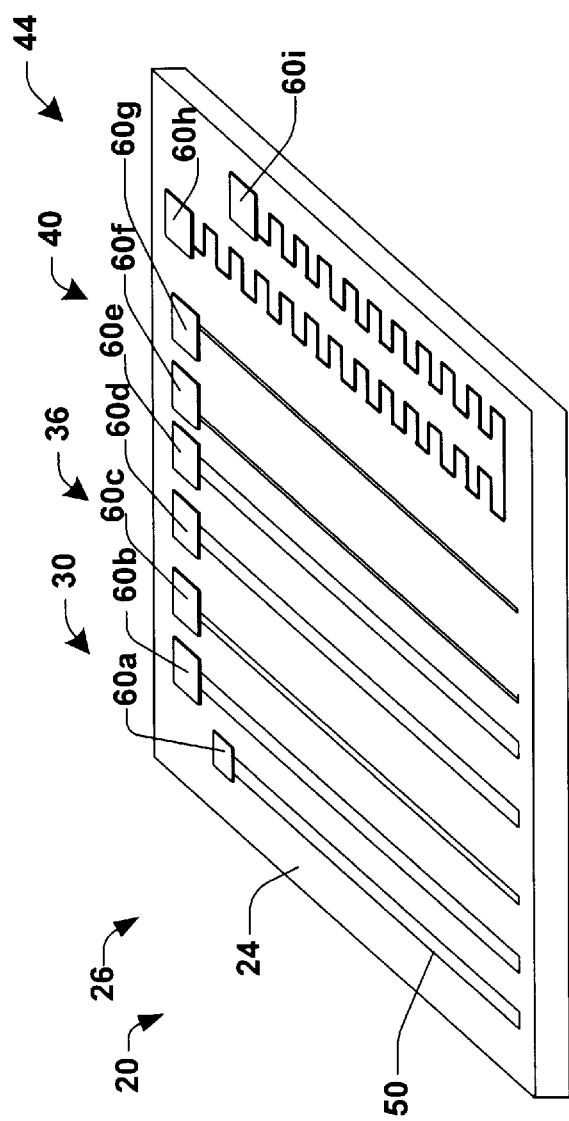
FIG. 15 is a perspective illustration of a substantially complete lubrication sensor in accordance with the present invention.

An initial patterning step 502 is performed to form the pH electrode 30 wherein standard photolithographic and deposition techniques are carried out to form the palladium pH electrode 52 shown in FIG. 9. Next as shown in FIG. 10, another photo lithographic/deposition step is performed to form the gold conductivity sensors 58, and the gold counter electrode 56 and the gold working electrode 54 of the electrochemical sensor 36 as seen in FIG. 11. FIG. 12 illustrates a third photo lithographic/deposition step 506 wherein a lift-off procedure is performed to apply platinum as is well known in the art. Platinum is difficult metal to etch and thus a lift-off procedure is preferred when working with platinum. This substantially completes the fabrication of the lubricant sensor 20 shown as shown in FIG. 1.

Although the present invention has been described primarily in the context of a preferred embodiment, it is to be appreciated that the present invention may be carried out in other embodiments. For instance, both top and bottom sides of the base 24 (FIG. 1) may include transducers 26 as compared to only a single side of the base 24. Such an embodiment enhances the functional scope of the present invention by doubling the amount of sensitive components of the lubricant sensor.

Although, the present invention has been described with respect to sensing and analysis of a lubricant, it is to be appreciated that the present invention provides for in situ monitoring, health assessment and future lube requirements assessment of any suitable fluid where knowledge thereof is desired.

What has been described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A multi-element fluid sensor system, comprising:
   at least two sensors, each sensor adapted to collect data relating to a fluid; and
   a data fusion processor operatively coupled to the at least two sensors, the data fusion processor processing the fluid data to at least compensate for fragmentation of information attributed to using the at least two sensors.

2. The system of claim 1, the at least two sensors being integrated onto a semiconductor base.

3. The system of claim 1, the data fusion processor condensing the fluid data.

4. The system of claim 1, the data fusion processor combining the fluid data.

5. The system of claim 1, the data fusion processor evaluating the fluid data.

6. The system of claim 1, the data fusion processor interpreting the fluid data.

7. The system of claim 1, the at least two sensors including a pH sensor.

8. The system of claim 1, the at least two sensors including a chemical sensor.

9. The system of claim 1, the at least two sensors including a conductivity sensor.

10. The system of claim 1, the at least two sensors including a temperature sensor.

11. The system of claim 1, the at least two sensors including a viscosity sensor.

12. The system of claim 1 providing for in situ monitoring of the fluid.

13. The system of claim 1, the fluid is one of: oil, grease, hydraulic fluid, cutting oil/cutting coolant, and biological fluid.

14. The system of claim 1 wherein the fluid is employed to lubricate at least one bearing of a dynamoelectric machine.

15. The system of claim 1 used in a forced lube system.

16. The system of claim 1 used in a gear box.

17. The system of claim 1 used in connection with hydrodynamic bearings.

18. The system of claim 1 used in connection with a bearing system.

19. A fluid sensing system, comprising:
at least a distributed set of two sensors integrated onto a semiconductor, base, the sensors respectively collecting data relating to a fluid; and
a data fusion processor also integrated onto the semiconductor base and being operatively coupled to the at least two sensors, the data fusion processor processing the fluid data to at least compensate for fragmentation and overlap of the fluid data attributed to using the at least two sensors.

20. The system of claim 19 used to provide in situ monitoring of the fluid.

21. The system of claim 19, the data fusion processor condensing the fluid data.

22. The system of claim 19, the data fusion processor combining the fluid data.

23. The system of claim 19, the data fusion processor evaluating the fluid data.

24. The system of claim 19, the data fusion processor interpreting the fluid data.

25. The system of claim 19 the at least two sensors including a pH sensor.

26. The system of claim 19 the at least two sensors including a chemical sensor.

27. The system of claim 19 the at least two sensors including a conductivity sensor.

28. The system of claim 19 the at least two sensors including a temperature sensor.

29. The system of claim 19 the at least two sensors including a viscosity sensor.

30. A distributed sensor system for in situ monitoring of a lubricant employed in a dynamoelectric machine, comprising:
a plural sensor means for collecting data for a plurality of parameters relating to the health of the lubricant; and
an algorithmic processing means for fusing the data to at least compensate for fragmentation and overlap of information between the data for the plurality of parameters.

31. A distributed sensor method for in situ monitoring a lubricant, in terms of any data, information or parameter that corresponds to a health state or quality level for said lubricant comprising the steps of:
using a distributed set of at least two sensors to collect a sum of data relating to the health state of the lubricant while the lubricant is being used; and
using a data via an algorithm implementation to at least compensate for any information fragmentation or fusion fusion system to process the data.

32. A lubrication sensor for assessing a quality, condition or health state in a lubrication application comprising:
a distributed set of at least two sensors, each sensor adapted to collect data relating to a lubricant; and
a data fusion processor operatively coupled to the at least two sensors, the data fusion processor processing the lubricant data via an algorithm implementation to at least compensate for fragmentation and/or overlap of information attributed to using the at least two sensors.

33. A lubrication sensor for use in connection with a dynamoelectric machine, comprising:
a set of distributed sensors including at least two of the following sensing devices adapted to collect data relating to a lubricant:
a temperature sensor for sensing temperature of the lubricant;
a viscosity sensor for sensing viscosity of the lubricant;
a chemical sensor for sensing chemical parameters of the lubricant;
a conductivity sensor for sensing electrical conductivity of the lubricant;
a pressure sensor for sensing lubricant pressure;
a shear viscosity sensor for sensing lubricant shear; and
a density sensor for sensing lubricant density; and
a pH sensor for sensing lubricant pH; and
a data fusion processor operatively coupled to the at least two sensing devices, the data fusion processor processing the lubricant data via an algorithm implementation to at least compensate for fragmentation and/or overlap of information attributed to using the at least two sensing devices.

34. A multi-element fluid sensor system having a distributed sensor configuration comprising:
a first sensor adapted to collect data relating to a fluid;
a second sensor substantially identical to the first sensor, the second sensor providing redundancy in collecting the fluid data via an algorithm implementation to at least compensate for any information fragmentation or fusion; and
a data fusion processor operatively coupled to the first and second sensors, the data fusion processor processing the fluid data;
wherein the employment of the second sensor facilitates fluid data reliability and accuracy.

* * * * *